US009777037B2

(12) United States Patent
Gravanis et al.

(10) Patent No.: US 9,777,037 B2
(45) Date of Patent: Oct. 3, 2017

(54) NEUROSTEROID COMPOUNDS

(75) Inventors: Achilleas Gravanis, Heraklion (GR); Theodora Calogeropoulou, Athens (GR); Elias Castanas, Heraklion (GR); Andreas Margioris, Heraklion (GR); Ioannis Charalambopoulos, Heraklion (GR); Nikolaos Avlonitis, Korydallos (GR); Vassilios Minas, Rodos (GR); Vasileia-Ismini Alexaki, Heraklion (GR); Christos Tsatsanis, Heraklion (GR); Michael N. Alexis, Athens (GR); Eumorphia Remboutsika, Vari (GR); Varvara Vergou, Athens (GR); Constantinos Neophytou, Nicosia (CY)

(73) Assignee: BIONATURE E. A. LTD. (CY)

( * ) Notice: Subject to any disclaimer, the term of this patent is extended or adjusted under 35 U.S.C. 154(b) by 690 days.

(21) Appl. No.: 12/665,569

(22) PCT Filed: Jun. 17, 2008

(86) PCT No.: PCT/GB2008/002067
§ 371 (c)(1),
(2), (4) Date: Jun. 1, 2010

(87) PCT Pub. No.: WO2008/155534
PCT Pub. Date: Dec. 24, 2008

(65) Prior Publication Data
US 2010/0234335 A1 Sep. 16, 2010

(30) Foreign Application Priority Data

Jun. 20, 2007 (GB) .................................. 0711948.0

(51) Int. Cl.
*A61K 31/58* (2006.01)
*C07J 21/00* (2006.01)

(52) U.S. Cl.
CPC .................................... *C07J 21/00* (2013.01)

(58) Field of Classification Search
CPC ....................................................... C07J 21/00
USPC .............................. 514/173; 540/456, 45, 64
See application file for complete search history.

(56) References Cited

U.S. PATENT DOCUMENTS

| 3,094,521 A | 6/1963 | Patchett et al. |
| 3,300,489 A | 1/1967 | Holden |
| 3,320,242 A | 5/1967 | Creger |
| 3,364,207 A | 1/1968 | Brown |
| 3,364,238 A | 1/1968 | Benn |
| 3,365,475 A | 1/1968 | Firestone et al. |
| 3,413,288 A | 11/1968 | Creger |
| 3,506,652 A | 4/1970 | Creger |
| 3,939,155 A | 2/1976 | Brown |
| 4,026,918 A | 5/1977 | Furst et al. |
| 4,054,563 A | 10/1977 | Anner et al. |
| 5,556,847 A | 9/1996 | Johnson et al. |

FOREIGN PATENT DOCUMENTS

| EP | 1 310 258 A1 | 5/2003 |
| GB | 1079840 | 8/1967 |
| WO | WO 9805337 | * 2/1998 |
| WO | WO 98/33506 | 8/1998 |
| WO | WO 2007/103162 A2 | 9/2007 |

OTHER PUBLICATIONS

Shull et al., "Reduction of 17alpha-hydroxy-20-keto steroids: Convenient synthesis of (E)-3beta-hydroxy-5,17(20)-pregnadiene 3-pivaloate and (Z)-3beta,16alpha-dihydroxy-5,17(20)-pregnadiene 3-pivaloate." J. Org. Chem., vol. 55, pp. 99-105, 1990.*
Baulieu et al., "Dehydroepiandrosterone (DHEA) and dehydroepiandrosterone sulfate (DHEAS) as neuroactive neurosteroids," PNAS (1998) vol. 95, pp. 4089-4091.
Bevins et al., "Irreversible Active-Site-Directed Inhibition of $\Delta^5$ -3-Ketosteroid Isomerase by Steroidal 17-β-Oxiranes. Evidence for Two Modes of Binding in Steroid-Enzyme Complexes," Biochem. and Biophys. Res. Comm. (1980) vol. 95, pp. 1131-1137.
Brown, "Some Steroidal Cyclic Ethers as Antiestrogen," J. of Medicinal Chem. (1967) vol. 10, pp. 546-551.
Charalampopoulos et al., "Dehydroepiandrosterone and allopregnanolone protect sympathoadrenal medulla cells against apoptosis vis antiapoptotic Bcl-2 proteins," PNAS. (2004) vol. 101, pp. 8209-8214.
Charalampopoulos et al., "Dehydroepiandrosterone Sulfate and Allopregnanolone Directly Stimulate Catecholamine Production via Induction of Tyrosine Hydroxylase and Secretion by Affecting Actin Polymerization," Endocrinology (2005) vol. 146, pp. 3309-3318.
Charalampopoulos et al., "G protein-associated, specific membrane binding sites mediate the neuroprotective effect of dehydroepiandrosterone," FASEB J. express article published online. 10.1096/fj.05-5078fje (2006) pp. 1-25.
Charalampopoulos et al., "G protein-associated, specific membrane binding sites mediate the neuroprotective effect of dehydroepiandrosterone," FASEB J. (2006) vol. 20, pp. 577-579.

(Continued)

Primary Examiner — Barbara P Badio
(74) Attorney, Agent, or Firm — J.A. Lindeman & Co., PLLC

(57) ABSTRACT

The present invention relates to novel neurosteroid derivatives with anti-apoptotic, neuroprotective and neurogenic properties that act on the nervous system as well as methods for making the same and their applications in the treatment and/or prevention or amelioration of neurodegenerative diseases related to neuronal apoptosis or neuronal injury, or conditions related to or resulting from apoptosis, including but not limited to Alzheimer's disease, Parkinson's disease, Huntington's disease, multiple sclerosis and amyotrophic lateral sclerosis (ALS), retinal degeneration and detachment, peripheral neuropathy caused by genetic abnormalities, diabetes, polio, herpes, AIDS and chemotherapy, brain trauma, or ischemia and stroke. The active compounds are represented by Formula (I): wherein $R^1$, $R^2$, $R^3$, $R^4$, $R^5$, $R^6$, $R^7$, A, B, X, Y and Z are defined in the description of the invention. The present invention also includes compositions which comprise one or more of the compounds of Formula (I).

4 Claims, 9 Drawing Sheets

(56) References Cited

OTHER PUBLICATIONS

Chen et al., "Unopposed Estrogen Therapy and the Risk of Invasive Breast Cancer," *Arch Intern Med.* (2006) vol. 166, pp. 1027-1032.
Chwastek et al., "'Alcoxypropargylation' Des Ceto-17 Steroides," *Tetrahedron* (1973) vol. 29, pp. 883-889.
Compagnone et al., "Neurosteroids: Biosynthesis and Function of These Novel Neuromodulators," *Frontiers in Neuroendocrinology* (2000) vol. 21, pp. 1-56.
Drefahl et al., "Umsetzung von Steroidketonen mit Sulfonium-Yliden," *Chemishe Berichte* (1964) pp. 3529-3535.
Fokialakis et al., "A New Class of Phytoestrogens: Evaluation of the Estrogenic Activity of Deoxybenzoins," *Chemistry & Biology* (2004) vol. 11, pp. 397-406.
Halabalaki et al., "Estrogenic Activity of Isoflavonoids from *Onobrychis ebenoides*," *Planta Med.* (2006) vol. 72, pp. 488-493.
Huang et al. "TRK Receptors: Roles in Neuronal Signal Transduction," *Ann. Rev. of Biochem.* (2003) vol. 72, pp. 609-642.
Krantic et al., "Molecular basis of programmed cell death involved in neurodegeneration," *TRENDS in Neurosciences* (2005) vol. 28, pp. 670-676.
Lardon et al., "Allopregnan-tetrol-(3β,17,20α,21). Bestandteile der Nebennierenrinde und verwandte Stoffe," *Helvetica Chimica Acta.* Fasciculus II, vol. XXXIV (1951) No. 84, pp. 756-767.
Lazennec et al., "Adenovirus-Mediated Delivery of a Dominant Negative Estrogen Receptor Gene Abrogates Estrogen-Stimulated Gene Expression and Breast Cancer Cell Proliferation," *Mol. Endocrin.* (1999) vol. 13, pp. 969-980.
Ling et al., "Synthesis and In Vitro Activity of some Epimeric 20α-Hydroxy, 20-0xime and Aziridine Pregnene Derivatives as Inhibitors of Human 17α-Hydroxylase/$C_{17,20}$-Lyase and 5α-Reductase," *Bioorganic & Medicinal Chemistry* (1998) vol. 6, pp. 1683-1693.
Mattson, "Apoptosis in Neurodegenerative Disorders," *Nature.* (2000) vol. 1, pp. 120-129.
Miljković et al., "Synthesis, Crystal and Molecular Structure, and Hyperconjugation of the Isomeric 17,20-Epoxy-17-Picolyl Derivatives of 5-Androstene and 5α-Androstane," *Tetrahedron* (1987) vol. 43, No. 3, pp. 631-641.
Suzuki et al., "Mitotic and neurogenic effects of dehydroepiandrosterone (OHEA) on human neural stem cell cultures derived from the fetal cortex," *PNAS* (2004) vol. 101, pp. 3202-3207.
Troisi at al., "Chemoselective construction of novel steroid derivatives," *Steroids* (2002) vol. 67, pp. 687-693.
Wang et al., "The Neurosteroid Allopregnanolone Promotes Proliferation of Rodent and Human Neural Progenitor Cells and Regulates Cell-Cycle Gene and Protein Expression" *The J. of Neurosc.* (2005) vol. 25, pp. 4706-4718.
International Preliminary Report on Patentability, International Application No. PCT/GB2008/002067 (corresponding to instant U.S. Appl. No. 12/665,569), dated Jan. 7, 2010 (Mühausen, D.).
International Search Report, International Application No. PCT/GB2008/002067 (corresponding to instant U.S. Appl. No. 12/665,569), dated Feb. 13, 2009 (Tabanella, S.).
Revised International Search Report, International Application No. PCT/GB2008/002067 (corresponding to instant application U.S. Appl. No. 12/665,569), dated May 25, 2009 (Tabanella, S.).
Revised International Search Report, International Application No. PCT/GB2008/002067 (corresponding to instant U.S. Appl. No. 12/665,569), dated Jul. 10, 2009 (Tabanella, S.).
Written Opinion of the International Searching Authority, International Application No. PCT/GB2008/002067 (corresponding to instant U.S. Appl. No. 12/665,569).
I. M. Gella, et.al.: "Steroidal Spirooxetanes. I. Synthesis and Antiandrogenic Properties of Some 17-Spirooxetanoandrostanes," *Pharmaceutical Chemistry Journal*, vol. 28, No. 8, pp. 561-565, 1994.
H. Chwastek et. al.: "'Alcoxypropargylation' des Ceto-17 Steroides-II: Proprietes et Configuration des Produits Obtenus," *Tetrahedron*, vol. 30, pp. 603-608, 1974.
Anderson et al., "Conformationally Constrained Anesthetic Steroids That Modulate GABAa Receptors," *J. med. Chem.* 43: 4118-4125 (2000).
Gella et al., "Steroid Spiro-Oxetanes. I. Synthesis and Antiandrogenic Qualities of Some 17-sprio-oxetane-andostenes," *Khimiko-Farmatsevticheskii Zhurnal* 8: 25-28 (1994), English summary only.
Katona et al., "Neurosteroid Analogues. 12. Potent enhancement of GABA-mediated chloride currents at GABAa receptors by ent-androgens," *Eur. J. Med. Chem.* 43:107-113 (2008).
Trost & Scudder, "New Synthetic Reactions, Stereoreversed Cyclobutanone Formation Uilizing Slenoxide as a Leaving Group," *J. Amer. Chem. Society* 99(23): 7601-7610 (1977).
Dvolaitzky et al., "Extension aromatisante du noyau D stéroïde (III). Transformation des époxy-17,20 prégnanes," *Bulletin de la Societe Chimique de France*, pp. 2793-2800 (1963).
Salamon et al., "Über Bestandteile der Nebennierenrinde und verwandte Stoffe. Herstellung und Umsetzungen der beiden isomeren 20,21-Oxydo-allopregnan-diole (3β, 17β); konfigurative Verknüpfung zweier Allo-pregnan-tetrole mit den entsprechenden Allo-pregnan-triolen," *Helvetica Chimica Acta* 30(7):1929-1945 (1947).
Florio et al., "Generation and Synthetic Applications of (3-Pyridinylchloromethyl)lithium," *J. Org. Chem.* 61 (12):4148-4150 (1996).
Shull et al., "Reduction of 17α-hydroxy-20-keto steroids: Convenient Synthesis of (E)-3β-hydroxy-5,17(20)- pregnadiene 3-Pivaloate and (Z)-3β,16α-Dihydroxy-5,17(20)-pregnadiene 3-Pivaloate," *J. Org. Chem.* 55(1):99-105 (1990).
Wenner et al., "Über Bestandteile der Nebennierenrinde und verwandte Stoffe. Umsetzungen des Androstanol-(3β)-ons-(17) mit Propargylalkohol und weitere Umfomiungen des entstehenden Acetylenderivates," *Helvetica Chimica Acta* 27(1):24-42 (1944).
Wang, "Neurosteroids and GABA-A receptor function," *Frontiers in Endocrinology* 2(44):1-23 (2011).
Communication pursuant to Article 94(3) EPC dated Apr. 17, 2013 for EP 08 762 391.4.

* cited by examiner

NEUROSTEROID COMPOUNDS

This is a National Phase Application in the United States of International Patent Application No. PCT/GB2008/002067, filed Jun. 17, 2008, which claims priority to Great Britain Patent Application No. 0711948.0, filed Jun. 20, 2007.

FIELD OF THE INVENTION

This invention pertains to neurosteroid compounds including spiro neurosteroid analogues without endocrine actions but with strong anti-apoptotic, neuroprotective and neurogenic properties, and their use in treating, preventing or ameliorating the symptoms of neuro-degenerative diseases, including, but not limited to, Alzheimer's disease, Parkinson's disease, Huntington's disease, multiple sclerosis and amyotrophic lateral sclerosis (ALS), retinal degeneration and detachment, and for the alleviation of benign forgetfulness and the memory impairment seen in senile dementia or in connection with neurodegenerative diseases. As a non-limiting example, the direct effect of the steroid compounds on the nervous system is presented. Additional indications of these neurosteroid compounds are the treatment of neuropathy and in particular peripheral neuropathy caused by genetic abnormalities and other conditions such as diabetes, polio, herpes AIDS, chemotherapy, brain trauma, or ischemia and stroke.

BACKGROUND OF THE INVENTION

The term neurodegeneration is used herein to refer to the progressive loss of nerve cells, occurring in aging and in neurodegenerative disorders, comprising but not limited to Alzheimer's, Parkinson's, Amyotrophic Lateral Sclerosis (ALS), Multiple Sclerosis and Huntington's disease, and in stroke, head and spinal trauma (*Nature Rev. Mol. Cell. Biol.* 1, 120 (2000)). Primarily, these diseases are characterized by chronic and progressive loss of neurons in discrete areas of the brain or the peripheral nerves, causing debilitating symptoms such as dementia, loss of memory, loss of sensory or motor capability, decreased overall quality of life and well-being, disability, and eventually, premature death. For most neurodegenerative diseases, currently there is little or no treatment; at best, treatments are symptomatic in nature and do not prevent or slow the progression of disease.

The term neuronal cell death by apoptosis is used herein to refer to the 'end-point' of many human neurological disorders, including but not limited to Alzheimer's, Parkinson's and Huntington's diseases, stroke/trauma, multiple and amyotrophic lateral sclerosis (*Trends Neurosci* 28, 670 (2006)). Apoptotic death of hippocampal and cortical neurons is responsible for the symptoms of Alzheimer's disease; death of midbrain neurons that use the neurotransmitter dopamine underlies Parkinson's disease; Huntington's disease involves the death of neurons in the striatum, which control body movements; and death of lower motor neurons manifests as amyotrophic lateral sclerosis. Additionally, brain ischemia and trauma induce necrosis of a small brain area, which then propagates neuronal cell loss by apoptosis to a larger brain area, due to the neurotoxic material released by the necrotic cells. Apoptotic neuronal cell loss is also observed in the ageing brain, as a physiological process.

The term natural neurosteroids is used herein to refer to molecules with the cholesterol backbone such as dehydroepiandrosterone (DHEA), or allopregnanolone, which are produced in the brain (*Proc Natl Acad Sci USA* 95, 4089 (1998)). Previous studies have shown that these endogenous, naturally occurring neurosteroids may protect neurons against cell apoptosis induced by neurotrophic factor deprivation (*Proc Natl Acad Sci USA* 101, 8209 (2004)). The neuroprotective, antiapoptotic effects of these neurosteroids occur at very low, nanomolar concentrations (1 nM), and are mediated by activation of specific membrane receptors and the subsequent production of anti-apoptotic Bcl-2 proteins (*FASEB J* 20, 577 (2006)). Furthermore, these natural neurosteroids at nanomolar concentrations stimulate the secretion and production of neuroprotective dopamine (*Endocrinology* 146, 3309 (2005)).

The adult central nervous system (CNS) is classically known as a structure with very limited regenerative capacity. However, several pathological conditions, e.g. ischemia, epilepsy and trauma, have been shown to upregulate neural stem cell activity in the sub-ventricular zone and the dentate gyrus. These findings suggest that signals are present throughout the adult brain, which allow limited neuronal regeneration to occur. This fundamental observation changes our view on neurodegeneration and the brain's regenerative capacity, giving us the potential ability to regenerate specific brain areas. Two naturally occurring neurosteroids (DHEA and allopregnanolone) have recently been shown to induce neurogenesis in various experimental models (*Proc Natl Acad Sci USA* 101, 3202 (2004) and *J Neurosci* 25, 4706 (2005)).

The lack of effective treatment for devastating neurodegenerative diseases has stimulated great interest in the development of neuroprotective means that can prevent or treat progressive loss of neural function leading to serious impairment and death. There is a sustained need for the development of new compounds for neural cell protection, repair and rescue, targeting neural cell apoptosis and survival or neurogenesis. Natural neurosteroids such as DHEA possess important neuro-protective and neurogenic properties in vitro and in vivo, in experimental animals. However, naturally occurring neurosteroids are metabolised in humans into estrogens, androgens or progestins which exert generalized and important endocrine side effects, including hormone-dependent neoplasias (*Front Neuroendocrinol* 21, 1 (2000)), thus limiting their clinical use.

GB 1,079,840 (1966) discloses 3β-hydroxy-17-spirooxyranyl-androst-5-ene as an intermediate in the synthesis of certain steroidal lactone compounds.

U.S. Pat. No. 3,320,242 (1967) discloses 17β,20-epoxy steroids and methods for their production. 17β,20-epoxy-17α-methylandrost-5-en-3β-ol (1) and 17β,20-epoxy-17α-methylandrost-4-en-3-one (2) are specifically claimed.

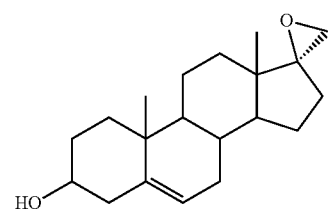

1

2

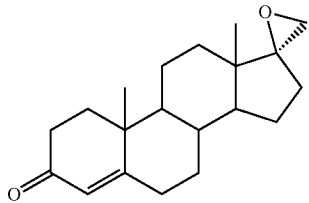

U.S. Pat. No. 3,300,489 (1967) discloses steroidal C-17 spirolactones and processes and intermediates used in the preparation thereof. Compounds 3 and 4 below are disclosed as intermediates.

3

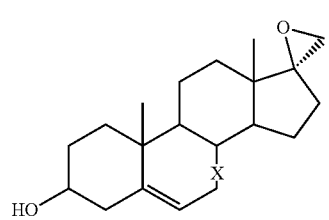

4

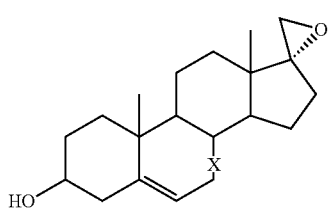

wherein X is a single C—C bond or a methylene group.

U.S. Pat. No. 3,413,288 (1968) and U.S. Pat. No. 3,506,652 disclose a process for the production of steroidal C-17 spirolactones using as an intermediate a steroidal epoxide compound having the formula

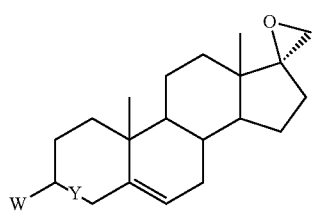

wherein Y represents a single bond when W is a hydroxyl group.

U.S. Pat. No. 3,365,475 (1968) discloses a process for the preparation of 17α-(3'-hydroxy-propyl)-4-androstene-3β,17β-diol which is useful in the preparation of steroidal 17-spirotetrahydrofurans which possess useful therapeutic properties as aldosterone inhibitors.

U.S. Pat. No. 3,364,238 (1968) discloses 3-oxygenated spiro[androstene-17,1'-cycloprop-2'-ene] and their 2',3'-dihydro derivatives of the structural formula

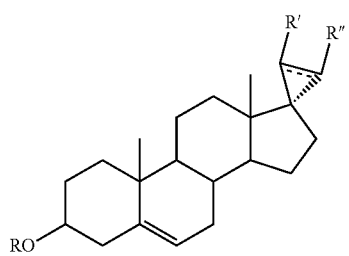

wherein R can be hydrogen or a lower alkanoyl radical, R' and R" can be hydrogen or a lower alkyl radical, and the dotted line indicates the optional presence of a double bond.

U.S. Pat. No. 4,026,918 (1977) describes the preparation of certain D-homosteroids that are said to have anti-inflammatory activity. (3β,11α,17α)-Spiro[androst-5-ene-17,2'-oxirane]-3,11-diol is disclosed as a chemical intermediate.

U.S. Pat. No. 4,054,563 (1977) discloses a process for the manufacture of 17-spiro-(2'-oxacyclopentane) steroid compounds of the general formula

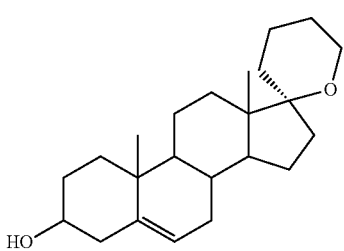

wherein $R_1$ represents a hydrogen atom or a lower alkyl group, which contain a double bond in the 5-position and a methyl group at the 10-position, or three double bonds in the position 1,3 and 5(10), and which can contain an additional double bond in the 9(11)-position. The compounds are said to be useful intermediates for preparing aldosterone antagonists.

WO 98/33506 discloses the use of certain compounds for inhibiting androgen synthesis, which are said to be useful in treating prostate cancer and benign prostatic hypertrophy. 17β,20β-Aziridinyl-pregn-5-en-3β-ol is one of the comparison compounds listed.

Helvetica Chimica Acta 34, 756-767 (1951) discloses reaction schemes according to which to 20α- and 20β-stereoisomers of 17,20-epoxy-17α-allopregnane-3β,21-diol diacetate may be formed.

In the Journal of Medicinal Chemistry 10(4), 546-551 (1967), the steroidal cyclic ether of formula 5 below is mentioned as an intermediate in the preparation of steroidal compounds having antiestrogenic properties.

5

Tetrahedron 29, 883-889 (1973) discloses certain steroid synthetic pathways in which (3β,17β)-3'-ethynyl spiro[androst-5-ene-17,2'oxiran]-3-ol acetate and (3β,17β)-3'-[(trimethylsilyl)ethynyl]spiro[androst-5-ene-17,2' oxiran]-3-ol acetate are intermediates.

Tetrahedron 43, 631-641 (1987) describes the preparation of the compounds of formula 6 and 7 below, as well as their 5α-H analogues.

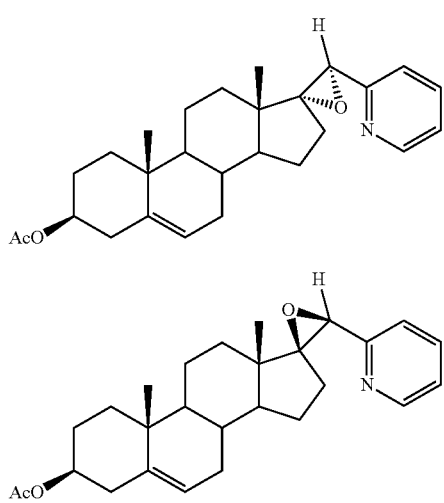

6

7

SUMMARY OF THE INVENTION

In a first aspect, the present invention relates to compounds of Formula I:

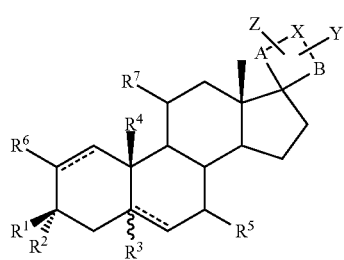

(I)

wherein $R^1$, $R^2$, $R^3$, $R^4$, $R^5$, $R^6$, $R^7$, A, B, X, Y and Z are as defined in the detailed description below; and pharmaceutically acceptable esters, salts and acid addition salts thereof.

In another aspect, this invention relates to a composition comprising at least one compound of Formula I or a pharmaceutically acceptable ester, salt or acid addition salt thereof, as active ingredient together with a pharmaceutically acceptable carrier, diluent or adjuvant.

In another aspect, this invention relates to a method of preventing or treating a neurodegenerative condition related to neuronal apoptosis or neuronal injury, comprising administering to a patient an effective amount of a compound of Formula I, or a pharmaceutically acceptable ester, salt or acid addition salt thereof. Said condition may, by way of example only, be any of Alzheimer's disease, Parkinson's disease, Huntington's disease, multiple sclerosis, amyotrophic lateral sclerosis (ALS), retinal degeneration, retinal detachment, peripheral neuropathy caused by genetic abnormalities, diabetes, polio, herpes, AIDS, brain trauma, ischemia and stroke.

In another aspect, this invention relates to a compound of Formula I, or a pharmaceutically acceptable ester, salt or acid addition salt thereof, for use in therapy.

In another aspect, this invention relates to a compound of Formula I, or a pharmaceutically acceptable ester, salt or acid addition salt thereof, for use in preventing or treating a neurodegenerative condition related to neuronal apoptosis or neuronal injury. Said condition may, for example, be any of those listed above.

In another aspect, this invention relates to the use of a compound of Formula I, or a pharmaceutically acceptable ester, salt or acid addition salt thereof, for the manufacture of a medicament for preventing or treating a neurodegenerative condition related to neuronal apoptosis or neuronal injury. Said condition may, for example, be any of those listed above.

In another aspect, this invention relates to the use of a compound of Formula I, or a pharmaceutically acceptable ester, salt or acid addition salt thereof, to control proliferation, differentiation, migration and regeneration of neural stem cells, and neural progenitor cells in different organs and tissues including the central nervous system and peripheral nervous system.

In another aspect, this invention relates to the use of a compound of Formula I, or a pharmaceutically acceptable ester, salt or acid addition salt thereof, for the control of proliferation, differentiation, migration and regeneration of epithelial, endothelial, mesenchymal, lymphoid, erythroid, and mononuclear cells.

In another aspect, this invention relates to the use of a compound of Formula I, or a pharmaceutically acceptable ester, salt or acid addition salt thereof, for binding, activating or inhibiting nerve growth factor (NGF) receptors, including TrkA and p75NTR receptors.

A better understanding of the invention will be obtained from the following detailed description of the article and the desired features, properties, characteristics, and the relation of the elements as well as the process steps, one with respect to each of the others, as set forth and exemplified in the description and illustrative embodiments.

Figure 1:
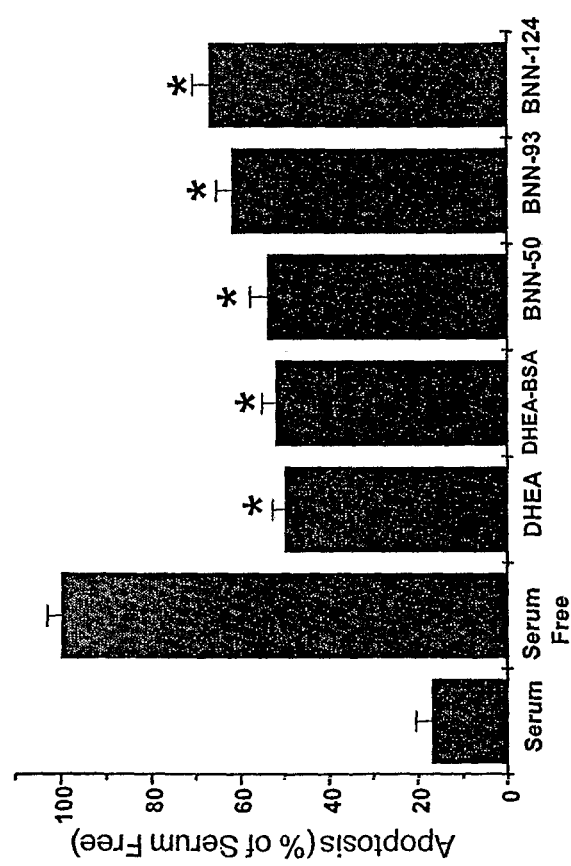
FIG. 1 is a bar chart showing the effect of several steroid compounds on apoptosis of neural-crest derived PC12 cells, in an experimental study using an assay technique.

More detailed discussion of the drawings appears in Examples 7-13 below.

DETAILED DESCRIPTION OF THE INVENTION

The present invention relates to compounds of Formula I

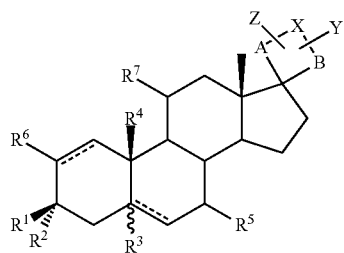

(I)

wherein $R^1$ is hydroxyl, alkoxy, alkanoyloxy, aminocarbonyloxy or alkoxycarbonyloxy;

$R^2$ is hydrogen, optionally substituted alkyl, optionally substituted alkenyl, optionally substituted alkoxyalkyl, optionally substituted aminoalkyl, cyano, optionally substituted cyanoalkyl, optionally substituted thiocyanoalkyl, isothiocyano, optionally substituted azidoalkyl, optionally substituted alkanoyloxyalkyl, optionally substituted arylalkyl, optionally substituted heteroarylalkyl, optionally substituted arylalkenyl, optionally substituted heteroarylalkenyl, optionally substituted aryl, optionally substituted arylkynyl, optionally substituted arylkylalkynyl, optionally substituted alkanoyloxyalkynyl, optionally substituted heteroaryloxyalkynyl, optionally substituted oxoalkynyl or a ketal thereof, optionally substituted cyanoalkynyl, optionally substituted heteroarylalkynyl, optionally substituted hydroxyalkynyl, optionally substituted alkoxyalkynyl, optionally substituted aminoalkynyl, optionally substituted acylaminoalkynyl, optionally substituted mercaptoalkynyl, optionally substituted hydroxyalkynyl dioic acid hemi-ester or a salt thereof, or optionally substituted alkynyloxyalkynyl;

or $R^1$ is oxygen and $R^2$ is alkyl or alkenyl or alkynyl group bonded to $R^1$ to form an oxygenated ring which can be optionally substituted;

$R^3$ is hydrogen, or when a double bond is present between C5 and C6 of the steroid ring system, then $R^3$ is not present;

$R^4$ is hydrogen or lower alkyl;

$R^5$ is hydrogen, amino, optionally substituted alkylamino, optionally substituted dialkylamino, optionally substituted alkenyl amino, optionally substituted dialkenylamino, optionally substituted alkynylamino, optionally substituted dialkynylamino, amido, thio, sulfinyl, sulfonyl, sulfonamido, halogen, hydroxyl, optionally substituted alkoxy, optionally substituted alkenyloxy, optionally substituted alkynyloxy alkyl, optionally substituted alkenyl, optionally substituted alkynyl, optionally substituted aryl, azido, optionally substituted heteroaryl, oxime =N—O—$R^8$, carboxymethyloxime, carboxyethyloxime, or carboxypropyloxime;

$R^6$ is hydrogen, amino, thio, sulfinyl, sulfonyl, sulfonamido, halogen, hydroxyl, optionally substituted alkoxy, optionally substituted alkyl, optionally substituted alkenyl, or optionally substituted alkynyl;

$R^7$ is hydrogen, amino, optionally substituted alkylamino, optionally substituted dialkylamino, optionally substituted alkenyl amino, optionally substituted dialkenylamino, optionally substituted alkynylamino, optionally substituted dialkynylamino, amido, thio, sulfinyl, sulfonyl, sulfonamido, halogen, hydroxyl, optionally substituted alkoxy, optionally substituted alkenyloxy, optionally substituted alkynyloxy alkyl, optionally substituted alkenyl, optionally substituted alkynyl, optionally substituted aryl, azido, optionally substituted heteroaryl, oxime =N—O—$R^8$, carboxymethyloxime, carboxyethyloxime, or carboxypropyloxime;

X is a valency bond, a methylene group (—CH$_2$—) or a heteroatom selected from oxygen, sulfur, or —NH, —S(O), —SO$_2$, —NR$^8$, —NC(O)R$^8$, —N-toluene-4-sulfonyloxy;

A is —(CH$_2$)$_n$—, a C$_{2-5}$ alkenylene group, or a C$_{2-5}$ alkynylene group, wherein n is an integer and can take the value of 0 or 1 or 2 or 3 or 4 or 5;

B is —(CH$_2$)$_y$—, a C$_{2-5}$ alkenylene group, or a C$_{2-5}$ alkynylene group, wherein y is an integer and can take the value of 1 or 2 or 3 or 4 or 5;

Y can be bonded to any carbon of the spirocyclic substituent at C17 of the steroid skeleton and is independently H, optionally substituted C$_{1-10}$ alkyl, an optionally substituted fused bicyclic ring system, an optionally substituted bridged bicyclic ring system, an optionally substituted bridged tricyclic ring system, optionally substituted C$_{2-10}$ alkenyl, optionally substituted C$_{2-10}$ alkynyl, optionally substituted aryl, optionally substituted arylalkyl, optionally substituted heteroaryl, optionally substituted heteroarylalkyl, formyl, carboxy, —NC(O)R$^8$, NC(S)R$^8$, —NR$^8$R$^9$, optionally substituted C(O)—W, optionally substituted C(O)O—W, or optionally substituted C(S)O—W;

Z can be bonded to any carbon of the spirocyclic substituent at C17 of the steroid skeleton and is independently H, optionally substituted C$_{1-10}$ alkyl, an optionally substituted fused bicyclic ring system, an optionally substituted bridged bicyclic ring system, an optionally substituted bridged tricyclic ring system, optionally substituted C$_{2-10}$ alkenyl, optionally substituted C$_{2-10}$ alkynyl, optionally substituted aryl, optionally substituted arylalkyl, optionally substituted heteroaryl, optionally substituted heteroarylalkyl, formyl, carboxy, —NC(O)R$^8$, NC(S)R$^8$, —NR$^8$R$^9$, optionally substituted C(O)—W, optionally substituted C(O)O—W, optionally substituted C(S)O—W;

Y and Z can be bonded to the same carbon of the spirocyclic substituent at C17

W is optionally substituted C$_{1-10}$ alkyl, optionally substituted heterocycloalkyl, an optionally substituted fused bicyclic ring system, an optionally substituted bridged bicyclic ring system, an optionally substituted bridged tricyclic ring system, optionally substituted $C_{2-10}$ alkenyl, optionally substituted heterocycloalkenyl, optionally substituted $C_{2-10}$ alkynyl, optionally substituted heterocycloalkynyl, optionally substituted aryl, or optionally substituted heteroaryl;

$R^8$ and $R^9$ are independently optionally substituted $C_{1-10}$ alkyl, optionally substituted heterocycloalkyl, an optionally substituted fused bicyclic ring system, an optionally substituted bridged bicyclic ring system, an optionally substituted bridged tricyclic ring system, optionally substituted $C_{2-10}$ alkenyl, optionally substituted heterocycloakenyl, optionally substituted $C_{2-10}$ alkynyl, optionally substituted heterocycloalkynyl, optionally substituted aryl, or optionally substituted heteroaryl;

and the dotted lines indicate that a single or double bond may be present.

The invention also relates to compositions comprising at least one compound of Formula I, or a pharmaceutically acceptable ester, salt or acid addition salt thereof, as active ingredient together with a pharmaceutically acceptable carrier, diluent or adjuvant.

The compounds of Formula I and their pharmaceutically acceptable esters, salts or acid addition salts can be used for treating, preventing or ameliorating the symptoms of neurodegenerative diseases, for the alleviation of benign forgetfulness and the memory impairment seen in senile dementia or in connection with neurodegenerative diseases, for the treatment of neuropathy due to several causes and for preventing apoptotic neuronal loss during brain trauma. Conditions that may be treated include, by way of example only, Alzheimer's disease, Parkinson's disease, Huntington's disease, multiple sclerosis, amyotrophic lateral sclerosis (ALS), retinal degeneration, retinal detachment, peripheral neuropathy caused by genetic abnormalities, diabetes, polio, herpes, AIDS, ischemia and stroke.

Preferred are embodiments of the invention wherein in Formula I above X is a methylene group, an oxygen atom or —NH. More preferably, X is an oxygen atom.

Also preferred are embodiments of the invention wherein in Formula I above a double bond is present between C5 and C6 of the steroid ring system; so that $R^3$ is not present.

Also preferred are embodiments of the invention wherein in Formula I above $R^1$=OH; $R^2$=$R^5$=$R^6$=$R^7$=Y=H and $R^4$=Me.

More preferred are embodiments of the invention wherein in Formula I above $R^1$=OH; $R^2$=$R^5$=$R^6$=$R^7$=Y=H, A=—(CH$_2$)$_n$— and B=—(CH$_2$)$_y$—; no double bond is present between C1 and C2 of the steroid ring system; a double bond is present between C5 and C6 of the steroid ring system, so that $R^3$ is not present; and $R^4$=Me. Yet more preferred are such compounds wherein n=0 and y=1.

Most preferred are embodiments of the invention wherein the compound of Formula I is selected from the following, including pharmaceutically acceptable esters, salts and acid addition salts thereof:

17β-spiro-[5-androsten-17,2'-oxiran]-3β-ol;
(20S)-3β,21-dihydroxy-17β,20-epoxy-5-pregnene;
(20S)-3β-hydroxy-17β,20-epoxy-20-(2-bromoethynyl)-5-androstene; and
3β,21-dihydroxy-17α,20-epoxy-5-pregnene.

In as much as the following compounds of Formula I above are known per se, they are not included within the scope of the present invention:

1) $R^1$=OH; $R^2$=$R^5$=$R^6$=$R^7$=Y=Z=H, A=—(CH$_2$)$_n$— and B=—(CH$_2$)$_y$—; no double bond is present between C1 and C2 of the steroid ring system; a double bond is present between C5 and C6 of the steroid ring system, so that $R^3$ is not present; $R^4$=Me; X=O, n=0 and y=1;

2) $R^1$ is hydroxy or alkoxy; $R^2$=$R^5$=$R^6$=$R^7$=Y=Z=H, A=—(CH$_2$)$_n$— and B=—(CH$_2$)$_y$—; no double bond is present between C1 and C2 of the steroid ring system; a double bond is present between C5 and C6 of the steroid ring system, so that $R^3$ is not present; $R^4$=Me; X=O, n=0 and y=3; wherein X is in the 17β-position;

3) 3',4',5',6'-tetrahydrospiro {androst-5-ene-17,2'-(2'H)-pyran]3β-ol, i.e. the compound of Formula I wherein $R^1$=OH; $R^2$=$R^5$=$R^6$=$R^7$=Y=Z=H, A=—(CH$_2$)$_n$— and B=—(CH$_2$)$_y$—; no double bond is present between C1 and C2 of the steroid ring system; a double bond is present between C5 and C6 of the steroid ring system, so that $R^3$ is not present; $R^4$=Me; X=O, n=0 and y=4; wherein X is in the 17β-position;

4) $R^1$ is hydroxy or alkanoyloxy; $R^2$=$R^5$=$R^6$=$R^7$=H, A=—(CH$_2$)$_n$— and B=—(CH$_2$)$_y$—; no double bond is present between C1 and C2 of the steroid ring system; a double bond is present between C5 and C6 of the steroid ring system, so that $R^3$ is not present; $R^4$=Me; X=—CH$_2$—, Y and Z are independently H or $C_1$-$C_7$ alkyl, n=0 and y=1;

5) $R^1$=OAc; $R^2$=$R^5$=$R^6$=$R^7$=Z=H, A=—(CH$_2$)$_n$— and B=—(CH$_2$)$_y$—; no double bond is present between C1 and C2 of the steroid ring system; $R^3$=H, or is not present and a double bond is present between C5 and C6 of the steroid ring system; $R^4$=Me; X=O, Y=2-pyridyl, n=0 and y=1;

6) 17β,20β-aziridinyl-pregn-5-en-3β-ol, i.e. the compound of Formula I wherein $R^1$=OH; $R^2$=$R^5$=$R^6$=$R^7$=Z=H; Y=CH$_3$; A=—(CH$_2$)$_n$— and B=—(CH$_2$)$_y$—; no double bond is present between C1 and C2 of the steroid ring system; a double bond is present between C5 and C6 of the steroid ring system, so that $R^3$ is not present; $R^4$=Me; X=—NH—, n=0 and y=1; wherein X is in the 17β-position;

7) (3β,11α,17α)-spiro[androst-5-ene-17,2'-oxirane]-3,11-diol, i.e. the compound of Formula I wherein $R^1$=OH; $R^2$=$R^5$=$R^6$=Y=Z=H; $R^7$=OH; A=—(CH$_2$)$_n$— and B=—(CH$_2$)$_y$—; no double bond is present between C1 and C2 of the steroid ring system; a doable bond is present between C5 and C6 of the steroid ring system, so that $R^3$ is not present; $R^4$=Me; X=O, n=0 and y=1; wherein $R^1$ is in the 11α-position and X is in the 17α-position;

8) 17,20-epoxy-17α-allopregnane-3β,21-diol diacetate, i.e. the compounds of Formula I wherein $R^1$=OAc; $R^2$=$R^3$=$R^5$=$R^6$=$R^7$=Z=H, A=—(CH$_2$)$_n$— and B=—(CH$_2$)$_y$—; no double bond is present between C1 and C2 of the steroid ring system; no double bond is present between C5 and C6 of the steroid ring system; $R^4$=Me; X=O, Y=—CH$_2$OAc, n=0 and y=1; and 9) (3β,17β)-3'-ethynyl spiro[androst-5-ene-17,2' oxiran]-3-ol acetate and (3β,17β)-3'-[(trimethylsilyl)ethynyl]spiro[androst-5-ene-17,2'oxiran]-3-ol acetate, i.e. the compounds of Formula I wherein $R^1$=OAc; $R^2$=$R^5$=$R^6$=$R^7$=Z=H, A=—(CH$_2$)$_n$— and B=—(CH$_2$)$_y$—; no double bond is present between C1 and C2 of the steroid ring system; a double bond is present between C5 and C6 of the steroid ring system, so that $R^3$ is not present; $R^4$=Me; X=O, Y=—C≡CH or —C≡C—SiMe$_3$, n=0 and y=1; wherein X is in the 17β-position.

Such compounds are known per se, although they are not known for use in, or associated with, diseases or conditions related to neuronal injury or neuronal cell death or the other conditions mentioned herein. Therefore these compounds are not excluded from the other aspects of the invention (compositions, methods, uses, etc.).

The following terms, alone or in combination, are defined herein as follows:

The term "alkyl" herein denotes a straight chain or branched chain or cyclic saturated hydrocarbon group. Preferable are $C_1$-$C_{16}$ alkyl groups. Unless otherwise specifically limited, an alkyl group may be unsubstituted, singly substituted or, if possible, multiply substituted, with substituent groups in any possible position. Unless otherwise specifically limited, a cyclic alkyl group includes monocyclic, bicyclic, tricyclic and polycyclic rings, for example adamantyl, norbornyl and related terpenes.

The term "heterocycloalkyl" herein denotes a cyclic hydrocarbon group containing one, two, three or four O, N or S atoms or combinations of O, N, S atoms, e.g. oxiranyl, oxetanyl, tetrahydrofuranyl, tetrahydro-2H-pyranyl, morpholinyl, aziridinyl, azetidinyl, pyrrolidinyl, piperidinyl, tetrahydrothiophenyl, tetrahydro-2H-thiopyranyl. Unless otherwise specifically limited, a heterocycloalkyl group may be unsubstituted, singly substituted or, if possible, multiply substituted, with substituent groups in any possible position.

The term "haloalkyl" herein denotes an alkyl group substituted with one or more halogens.

The term "alkenyl", alone or in combination, herein denotes a straight chain or branched chain or cyclic unsaturated hydrocarbon group which contains at least one carbon-carbon double bond. Unless otherwise specifically limited, an alkenyl group may be unsubstituted, singly substituted or, if possible, multiply substituted, with substituent groups in any possible position. Preferable are $C_2$-$C_{16}$ alkenyl groups. Alkenyl is meant to include the allenyl group, which possesses two consecutive double bonds.

The term "heterocycloalkenyl" herein denotes a cyclic unsaturated hydrocarbon group containing at least one carbon-carbon double bond containing one, two, three or four O, N or S atoms or combinations of O, N, S atoms. Unless otherwise specifically limited, a heterocycloalkenyl group may be unsubstituted, singly substituted or, if possible, multiply substituted, with substituent groups in any possible position.

The term "alkynyl", alone or in combination, herein denotes a straight chain or branched chain or cyclic unsaturated group which contains at least one carbon-carbon triple bond. Unless otherwise specifically limited, an alkynyl group may be unsubstituted, singly substituted or, if possible, multiply substituted, with substituent groups in any possible position. Preferable are $C_2$-$C_{16}$ alkynyl groups.

The term "aryl", alone or in combination, herein denotes an aromatic group which contains at least one ring with conjugated π electrons, carbocyclic aryl groups, and biaryl groups which may be unsubstituted, singly substituted or, if possible, multiply substituted, with substituent groups in any possible position. Preferable are $C_2$-$C_{10}$ aryl groups. Typical aryl groups include phenyl, naphthyl, phenanthryl, anthracyl, indenyl, azulenyl, biphenyl, biphenylenyl and fluorenyl groups.

The term "biaryl" represents aryl groups substituted by other aryl groups.

The term "carbocyclic aryl" refers to groups wherein the ring atoms on the aromatic ring are carbon atoms.

The term "thio" herein denotes —$SR^{10}$, where $R^{10}$ is hydrogen, alkyl, alkenyl, alkynyl, aryl, aryl alkyl or heteroaryl, all of which may be optionally substituted.

The term "sulfinyl" herein denotes —$SOR^{10}$, where $R^{10}$ is hydrogen, alkyl, alkenyl, alkynyl, aryl, arylalkyl or heteroaryl, all of which may be optionally substituted.

The term "sulfonyl" herein denotes —$SO_2R^{10}$, where $R^{10}$ is hydrogen, alkyl, alkenyl, alkynyl, aryl, arylalkyl or heteroaryl, all of which may be optionally substituted.

The term "sulfonamido" herein denotes —$SO_2NR^{10}R^{11}$, wherein $R^{10}$ and $R^{11}$ are independently hydrogen, alkyl, alkenyl, alkynyl, aryl, arylalkyl or heteroaryl, all of which may be optionally substituted.

The term "optionally substituted" or "substituted" refers to groups substituted by a below described substituent group in any possible position. Substituent groups for the above moieties useful in the invention are those groups that do not significantly diminish the biological activity of the inventive compound. Substituent groups that do not significantly diminish the biological activity of the inventive compound include, for example, lower alkyl (acyclic and cyclic), aryl (carbocyclic aryl and heteroaryl), alkenyl, alkynyl, alkoxy, halo, haloalkyl, amino, alkylamino, dialkylamino, mercapto, alkylthio, alkylsulfinyl, alkylsulfonyl, nitro, alkanoyl, alkanoyloxy, alkanoyloxyalkanoyl, alkoxycarboxy, carbalkoxy, carboxamido, formyl, carboxy, hydroxy, cyano, azido, isocyano, isothiocyano, oxime, keto and cyclic ketals thereof, alkanoylamido, heteroaryloxy, O-aroyl, OalkylOH, OalkenylOH, OalkynylOH, OalkylN$X_1X_2$, OalkenylN$X_1X_2$, OalkynylN$X_1X_2$, NH-acyl, NH-aroyl, $CF_3$, $COOX_3$, $SO_3H$, $PO_3X_1X_2$, $OPO_3X_1X_2$, $SO_2NX_1X_2$, $CONX_1X_2$, wherein $X_1$ and $X_2$ each independently denotes H or alkyl or alkenyl or alkynyl, or $X_1$ and $X_2$ together comprise part of a heterocyclic ring having about 4 to about 7 ring atoms and optionally one additional heteroatom selected from O, N or S, or $X_1$ and $X_2$ together comprise part of an imide ring having about 5 to 6 ring atoms and $X_3$ denotes H, alkyl, alkenyl, alkynyl, hydroxy-lower alkyl or alkyl-N$X_1X_2$, The term "lower" is referred to herein in connection with organic radicals or compounds containing one up to and including six carbon atoms. Such groups may be straight chain, branched chain, or cyclic.

The term "heteroaryl" refers to carbon containing 5-14 membered cyclic unsaturated radicals containing one, two, three or four O, N or S atoms and having 6, 10 or 14π electrons delocalized in one or more rings, e.g., thienyl, benzo[b]thienyl, naphtha[2,3-b]thienyl, thianthrenyl, furyl, pyranyl, isobenzofuranyl, chromenyl, xanthenyl, phenoxanthinyl, 2H-pyrrolyl, imidazolyl, pyrazolyl, pyridyl, pyrimidinyl, pyridazinyl, indolizinyl, isoindolyl, 3H-indolyl, indoyl, indazolyl, purinyl, 4H-quinolizinyl, isoquinolyl, quinolyl, phthazinyl, napthyridinyl, quinazolinyl, cinnolinyl, pterdinyl, 5aH-carbazoyl, carbozoyl, beta-carbolinyl, phenanthridinyl, acrindinyl, oxazolyl, pyrimidinyl, benzimidazolyl, triazolyl, each of which may be optionally substituted as discussed above.

The present invention also includes pharmaceutically acceptable esters and salts of the compounds of Formula I, including acid addition salts.

Those skilled in the art will recognize that stereocentres exist in compounds of Formula I. Accordingly, the present invention includes all possible stereoisomers and geometric isomers of Formula I as a mixture or as pure diastereomers. When a compound of Formula I is desired as a single diastereomer, it may be obtained either by resolution of the final product or by stereospecific synthesis from either isomerically pure starting material or any convenient intermediate.

Included within the scope of the present invention (compounds, pharmaceutical compositions, methods, uses, etc.) are the crystalline forms (e.g. polymorphs), enantiomeric forms and tautomers of the compounds of Formula I as defined herein and of the pharmaceutically acceptable salts or acid addition salts thereof.

The compounds of Formula I may be prepared from commercially available steroid compounds using conventional synthetic reactions familiar to those skilled in the art. Preferred embodiments of the invention wherein X is an oxygen atom can be prepared from the important intermediate (20S)-3β-(t-butyldiphenylsilyloxy)-21-hydroxy-17β,20-epoxy-5-pregnene employing a series of synthetic steps in the appropriate order including but not limited to oxidation, Wittig reaction, reduction, hydrogenation, oxime formation, halogenation, carbon-carbon coupling reactions and removal of the protective group at C3. Suitable hydroxyl protective groups other than the t-butyldiphenylsilyloxy, can be employed. The Examples below are illustrative of some of the preparative techniques that may suitably be employed.

The compounds of the present invention act on the CNS and the peripheral nervous system. Desirable objects of the pharmaceutical compositions and methods of this invention are the treatment and/or prevention of neurodegenerative diseases or disorders related to neuronal apoptosis or neuronal injury, such as, but not limited to, Alzheimer's disease, Parkinson's disease, Huntington's disease, multiple sclerosis and amyotrophic lateral sclerosis (ALS), retinal degeneration and detachment, peripheral neuropathy caused by genetic abnormalities, diabetes, polio, herpes, AIDS and chemotherapy, brain trauma, or ischemia and stroke, or any other condition resulting in degeneration and/or apoptosis of neural cells in the central or the peripheral nervous system.

The term "treat" or "treatment" as used herein refers to any treatment of a disorder or disease related to neuronal apoptosis or neuronal injury in a subject and includes, but is not limited to, preventing the disorder or disease from occurring in a subject who has not yet been diagnosed as having the disorder or disease, inhibiting the disorder or disease, for example arresting the development of the disorder or disease, relieving the disorder or disease, for example, causing regression of the disorder or disease, or relieving the condition caused by the disease or disorder, for example, stopping the symptoms of the disorder or disease.

Formulations of the preSent invention may be administered in standard manner for the treatment of the indicated diseases, including but not limited to oral, parenteral, sublingual, transdermal, rectal, or administration via inhalation or via buccal administration. Additionally, compositions of the present invention may be formulated for parenteral administration by injection or continuous infusion. The composition according to the invention may be formulated as a slow release form or as a depot preparation. The route of administration may be any route that effectively transports the active compound to the desired site for it to exert its antiapoptotic effects. Any person trained in the art may extend the former description to any other method of administration, not harming the recipient person.

The pharmaceutical compositions of this invention are prepared in conventional dosage unit forms by incorporating an active compound of the invention or a mixture of such compounds, with nontoxic pharmaceutical carrier according to accepted procedures in a nontoxic amount sufficient to produce the desired pharmacodynamic activity in a subject, animal or human. Preferably, the composition contains the active ingredient in an active, but nontoxic amount which depends on the specific biological activity desired and the condition of the patient.

The pharmaceutical carrier employed may be, for example, either a solid or a liquid. Representative solid carriers are lactose, terra alba, sucrose, talc, gelatin, agar, pectin, acacia, magnesium stearate, stearic acid, microcrystalline cellulose, polymer hydrogels and the like. Typical liquid carriers are propylene glycol, aqueous solutions of β-cyclodextrins, syrup, peanut oil and olive oil and the like emulsions. Similarly, the carrier or diluent may include any time-delay material well known to the art, such as glycerol monostearate or glycerol distearate alone or with wax, microcapsules, microspheres, liposomes, and/or hydrogels.

In the case of a solid carrier, the preparation can be plain milled, micronized or nanosized, in oil, tableted, placed in a hard gelatin or enteric-coated capsule in micronized powder or pellet form, or in the form of a troche, lozenge, or suppository. In the case of a liquid carrier, the preparation can be in the form of a liquid, such as an ampule, or as an aqueous or nonaqueous liquid suspension mixed with pharmaceutically acceptable preservatives and the like. When low dosages are required, nasal spray, sublingual administration and timed released skin patches are also suitable pharmaceutical forms for topical administration.

Some specific compounds of Formula I are listed below, the synthesis of which was performed in accordance with the Example section set forth below. These Examples are provided for a better understanding of the invention, and are not to be taken as limiting the scope of the invention in any way.
1) 17β-spiro-[5-androsten-17,2'-oxiran]-3β-ol ("BNN-50")
2) (20S)-3β,21-dihydroxy-17β,20-epoxy-5-pregnene ("BNN-124")
3) (20S)-3β-hydroxy-17β,20-epoxy-20-(2-bromoethynyl)-5-androstene
4) 3β,21-dihydroxy-17α,20-epoxy-5-pregnene ("BNN-93")

EXPERIMENTAL SECTION

NMR spectra were recorded on a Bruker AC 300 spectrometer operating at 300 MHz for $^1$H and 75.43 MHz for $^{13}$C. $^1$H NMR spectra are reported in units of δ relative to internal CHCl$_3$ at 7.24 ppm. $^{13}$C NMR shifts are expressed in units of S relative to CDCl$_3$ at 77.0 ppm. $^{13}$C NMR spectra were proton noise decoupled. All NMR spectra were recorded in CDCl$_3$. Silica gel plates (Merck F254) were used for thin layer chromatography. Chromatographic purification was performed with silica gel (200-400 mesh).

Example 1

Preparation of 17β-spiro-[5-androsten-17,2'-oxiran]-3β-ol

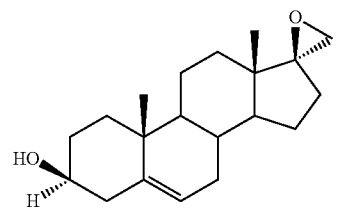 [SMILES: C[C@]12CC[C@H](O)CC1=CCC1C2CC[C@@]2(C)C1CC[C@@]21CO1]

To a solution of dehydroepiandrosterone (500 mg, 1.73 mmol) in anhydrous DMF (10 mL), trimethylsulfonium iodide (530 mg, 2.60 mmol) and t-BuOK (292 mg, 2.60 mmol) were added at 0° C., and the resulting mixture was stirred at room temperature for 2 hours. After completion of the reaction water was added and the resulting mixture was extracted with diethyl ether. The organic layer was washed with brine, then dried with anhydrous $Na_2SO_4$ and the solvent was evaporated in vacuo. The residue was purified by flash column chromatography (elution solvent: petroleum ether 40°-60° C./acetone 8:2), to obtain the compound of Example 1 as a white crystalline solid. Yield: 310 mg (59%); m.p. 170-173° C.; $[\alpha]_D^{20}$=−72.80° (C=0.00125 g/mL, $CHCl_3$); $^1H$ NMR ($CDCl_3$) δ: 5.35 (s, 1H, 6-CH), 3.47-3.54 (m, 1H, 3a-H), 2.89 (d, J=4.88 Hz, 1H), 2.59 (d, J=4.88 Hz, 1H), 2.2-0.9 (m, 20H), 1.00 (s, 3H, 18-$CH_3$), 0.88 (s, 3H, 19-$CH_3$), $^{13}C$ NMR ($CDCl_3$) δ: 14.14, 19.38, 20.41, 23.58, 28.99, 31.35, 31.54, 31.99, 33.84, 36.59, 37.23, 39.89, 42.18, 50.14, 53.12, 53.63, 70.52, 71.59, 121.21, 140.88.

Example 2

Preparation of (20S)-3β,21-dihydroxy-17β,20-epoxy-5-pregnene

17α-Vinyl-5-androstene-3β,17β-diol

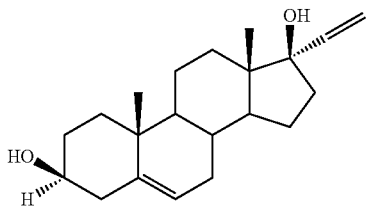 [SMILES: C=C[C@]1(O)CCC2C3CC=C4C[C@@H](O)CC[C@]4(C)C3CC[C@@]21C]

To a solution of dehydroepiandrosterone (250 mg, 0.87 mmol) in anhydrous tetrahydrofuran (7 mL) was added dropwise at −78° C. a solution of vinyl magnesium bromide (1 M in tetrahydrofuran, 4.35 mL, 4.35 mmol) and the resulting mixture was stirred at room temperature for 12 h. After completion of the reaction saturated ammonium chloride was added and the resulting mixture was extracted with ethyl acetate. The organic layer was washed with brine, then dried with anhydrous $Na_2SO_4$ and the solvent was evaporated in vacuo. The residue was purified by flash column chromatography (elution solvent: cyclohexane/acetone 9:1), to obtain 17α-vinyl-5-androstene-3β,17β-diol as a white crystalline solid.

Yield: 200 mg (74%); m.p. 180-183° C.; $^1H$ NMR ($CDCl_3$) δ: 6.01 (q, J=10.99 Hz; 1H), 5.31 (s, 1H,), 5.09 (t, J=10.99 Hz, 2H), 3.47-3.51 (m, 1H, 3a-H), 1.18-2.48 (m, 21H), 0.99 (s, 3H), 0.90 (s, 3H); $^{13}C$-NMR ($CDCl_3$) δ: 13.95, 19.38, 20.64, 23.65, 31.61, 32.09, 32.58, 36.14, 37.24, 42.22, 46.10, 49.95, 50.31, 71.69, 84.18, 111.87, 121.31, 140.82, 143.02.

3β,17β-dihydroxy-20,21-epoxy-5-androstene

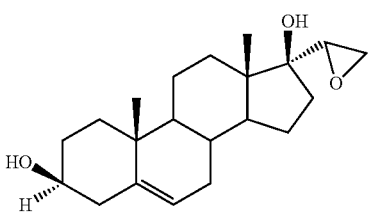 [SMILES: C[C@]12CC[C@H](O)CC1=CCC1C2CC[C@@]2(C)C1CC[C@@]2(O)C1CO1]

To a solution of 17α-vinyl-5-androstene-3β,17β-diol (150 mg, 0.47 mmol) in anhydrous dichloromethane (5 mL), vanadium acetylacetonate (2.5 mg, 0.01 mmol) and t-butylhydroperoxide 70% (0.14 mL, 0.94 mmol). were sequentially added at −10° C. The resulting mixture was stirred at 0° C. for 12 h. After completion of the reaction the mixture was diluted with dichloromethane and the organic layer was extracted with $H_2O$, saturated $Na_2SO_3$ and brine and then was dried with anhydrous $Na_2SO_4$ and the solvent was evaporated in vacuo. The residue was purified by flash column chromatography (elution solvent: dichloromethane/ethyl acetate 6:4), to obtain 3β,17β-dihydroxy-20,21-epoxy-5-androstene as a white crystalline solid. Yield: 50 mg (32%); m.p. 165-168° C.; $[\alpha]_D^{20}$=−53.10° (C=0.00113 g/mL, $CHCl_3$); $^1H$-NMR ($CDCl_3$) δ: 5.35 (s, 1H), 3.08 (t, J=4.27 Hz, 1H), 2.87 (q, J=3.05 Hz, 1H), 2.76 (d, J=3.05 Hz, 1H), 1.24-2.29 (m, 19H), 1.02 (s, $3H_3$), 0.92 (s, 3H); $^{13}C$ NMR ($CDCl_3$) δ: 13.91, 19.38, 20.54, 24.04, 31.61, 32.38, 36.01, 36.59, 37.27, 42.22, 43.19, 45.48, 50.11, 51.44, 51.79, 54.83, 56.22, 71.69, 79.68, 121.24, 140.81.

(20S)-3β,21-dihydroxy-17β,20-epoxy-5-pregnene

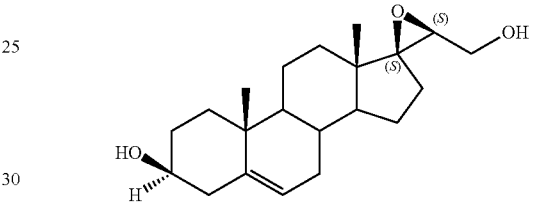

To a solution of 3β,17β-dihydroxy-20,21-epoxy-5-androstene (40 mg, 0.12 mmol) in anhydrous MeOH (2 mL) was added $K_2CO_3$ (41 mg, 0.3 mmol) and the resulting mixture was stirred at room temperature for 12 hours. After completion of the reaction the mixture was diluted with ethyl acetate and the organic layer was extracted with $H_2O$ and brine and then was dried with anhydrous $Na_2SO_4$. The solvent was evaporated in vacuo and the residue was purified by flash column chromatography (elution solvent: dichloromethane/ethyl acetate 3:1), to obtain (20S)-3β,21-dihydroxy-17β,20-epoxy-5-androstene as a white crystalline solid. Yield: 32 mg (80%); $[\alpha]_D^{20}$=−70.00° (C=0.0009 g/mL, $CHCl_3$); $^1H$ NMR ($CDCl_3$) δ: 5.28 (s, 1H), 3.63 (q, J=4.27 Hz, 1H), 3.40-3.49 (m, 2H), 3.12 (q, J=3.66 Hz), 1.36-2.21 (m, 21H), 0.95 (s, 3H), 0.81 (s, 3H).

Example 3

Preparation of (20S)-3β-hydroxy-17β,20-epoxy-20-(2-bromoethynyl)-5-androstene

3β-(t-butyldiphenylsilyloxy)-5-androstene-17-one

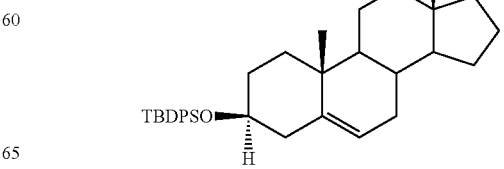

To a solution of dehydroepiandrosterone (1 g, 3.47 mmol) in dry DMF (20 mL) was added at 0° C. imidazole (591 mg, 8.981 mmol). The resulting mixture was stirred for 30 minutes, t-butyl-diphenylsilyl chloride (2.22 mL, 8.681 mmol) was added, and the reaction was stirred overnight at 50° C. After completion of the reaction 20 mL saturated NH$_4$Cl was added, the resulting mixture was stirred for 30 minutes and the solvent was evaporated in vacuo. To the residue was added ethyl acetate and the organic layer was extracted with H$_2$O and brine and then was dried with anhydrous Na$_2$SO$_4$. The solvent was evaporated in vacuo and the residue was recrystallised with EtOH/petroleum ether 40-60° C. After filtration of the solid the mother liquor was purified by flash column chromatography (elution solvent: cyclohexane/EtOAc 95:5). Yield: 1282 mg (70%); $^1$H NMR (CDCl$_3$) δ: 7.80-7.74 (m, 4H), 7.42-7.40 (m, 6H), 5.22 (bs, 1H), 3.62 (bs, 1H), 2.50-0.90 (m, 19H), 1.14 (s, 9H), 1.07 (s 3H), 0.89 (s, 3H).

3β-(t-butyldiphenylsilyloxy)-17α-vinyl-5-androstene-17β-ol

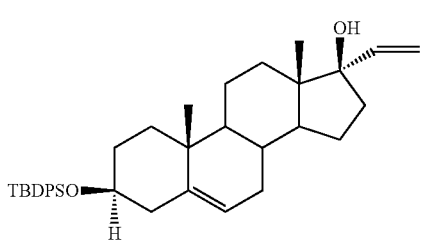

To a solution of 3β-(t-butyldiphenylsilyloxy)-5-androstene-17-one (861 mg, 1.635 mmol) in dry THF (30 mL) was added dropwise at −78° C. a solution of vinyl magnesium bromide 1M in THF (16.35 mL, 16.35 mmol). The mixture was stirred at −20° C. for two hours and then overnight at room temperature. Saturated NH$_4$Cl (25 mL) was poured into the reaction vessel, the mixture was stirred for 30 minutes, and the solvent was evaporated in vacuo. The residue was purified by flash column chromatography (elution solvent: cyclohexane/EtOAc 95:5) to afford 3β-(t-butyldiphenylsilyloxy)-17α-vinyl-5-androstene-17β-ol in 60% yield.

$^1$H NMR (CDCl$_3$) δ: 7.67-7.65 (m, 4H), 7.39-7.25 (m, 6H), 6.00 (dd, J=10.98, 17.70 Hz, 1H), 5.14-5.05 (m, 3H), 3.50-3.46 (m, 1H), 2.32-0.87 (m, 19H), 1.05 (s, 9H), 0.99 (s 3H), 0.88 (s, 3H).

3β-(t-butyldiphenylsilyloxy)-17β-hydroxy-20,21-epoxy-5-androstene

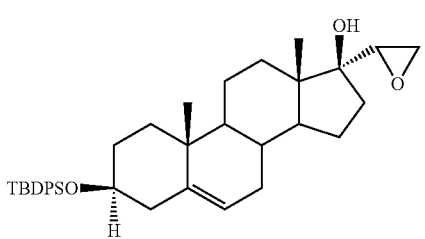

To a solution of 3β-(t-butyldiphenylsilyloxy)-17α-vinyl-5-androstene-17β-ol (191 mg, 0.345 mmol) in dry dichloromethane (3.7 mL) were sequentially added at −10° C. VO(acac)$_2$ (1.95 mg, 0.021 eq.) and t-BuOOH 0.2936 mL (0.69 mmol, ~2.35 M sol. in 1,2-dichloroethane). The reaction mixture was stirred at 0° C. overnight, and then was diluted with 15 mL dichloromethane, washed with water, Na$_2$SO$_3$, and brine (1×10 mL). The organic layers were dried over anhydrous. Na$_2$SO$_4$, and the solvent was evaporated in vacuo. The residue was purified by flash column chromatography (elution solvent: petroleum ether: diethyl ether 95:5) to afford 3β-(t-butyldiphenylsilyloxy)-17β-hydroxy-20,21-epoxy-5-androstene. Yield: 127 mg (65%); $^1$H NMR (CDCl$_3$) δ: 7.73-7.69 (m, 4H), 7.43-7.36 (m, 6H), 5.17-5.15 (m, 1H), 3.59-3.53 (m, 1H), 3.09-3.07 (m, 1H), 2.89-2.87 (m, 1H), 2.76-2.73 (m, 1H), 2.42-2.34 (m, 1H), 2.2.1-0.84 (m, 18H), 1.09 (s, 9H), 1.04 (s, 3H), 0.93 (s, 3H).

(20S)-3β-(t-butyldiphenylsilyloxy)-21-hydroxy-17β, 20-epoxy-5-pregnene

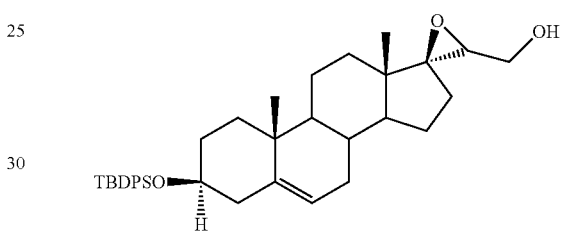

To a solution of 3β-(t-butyldiphenyl silyl oxy)-17β-hydroxy-20,21-epoxy-5-androstene (51 mg, 0.0894 mmol) in a mixture of dry MeOH:dry THF (1.5:1.5 mL) was added at room temperature K$_2$CO$_3$ (31 mg, 0.2235 mmol). The reaction mixture was stirred at room temperature overnight, and then was diluted with EtOAc (5 mL) and washed with water and brine. The organic layers were dried over anhydrous Na$_2$SO$_4$, and the solvent was evaporated in vacuo. The residue was purified by flash column chromatography (elution solvent: cyclohexane:EtOAc 8:2) to afford (20S)-3β-(t-butyldiphenylsilyloxy)-21-hydroxy-17β,20-epoxy-5-androstene in 80% yield.

$^1$H NMR (CDCl$_3$) δ: 7.69-7.65 (m, 4H), 7.42-7.33 (m, 6H), 5.13-5.12 (m, 1H), 3.76 (dd, J=3.66, 12,20 Hz, 1H) 3.58-3.49 (m, 2H), 3.17 (dd, J=4.27, 6.71 Hz, 1H), 2.37-2.29 (m, 1H), 2.17-2.11 (m, 1H), 1.99-0.81 (m, 17H), 1.05 (s, 9H), 0.99 (s 3H), 0.85 (s, 3H).

(20S)-3β-(t-butyldiphenylsilyloxy)-17β,20-epoxy-5-androstene-21-carboxaldehyde

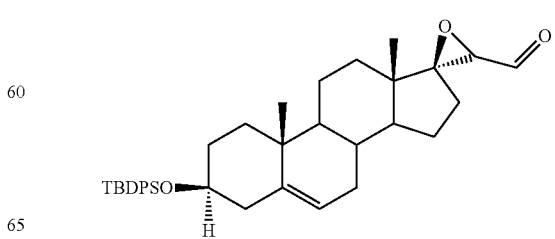

To a solution of 3β-(t-butyldiphenylsilyloxy)-21-hydroxy-17β, 20-epoxy-5-androstene (51 mg, 0.0894 mmol) in dry dichloromethane (5 mL) was added at 0° C. Dess-Martin Periodinane (75.8 mg, 0.1782 mmol).The mixture was stirred at room temperature for 1 hour. The reaction mixture was diluted with diethyl ether (10 mL), and washed with a mixture of saturated NaHCO₃: saturated Na₂S₂O₃ 1:2 (10 mL), saturated NaHCO₃ (10 mL), and brine (10 mL). The organic layers were dried over anhydrous Na₂SO₄, and the solvent was evaporated in vacuo. The residue was purified by flash column chromatography (elution solvent: cyclohexane:EtOAc 9:1) to afford (20S)-3β-(t-butyldiphenylsilyloxy)-17β,20-epoxy-5-androstene-21-carboxaldehyde. Yield 46.6 mg (98%). ¹H NMR (CDCl₃) d: 9.26 (d, J=5.49 Hz, 1H), 7.69-7.67 (m, 4H), 7.42-7.34 (m, 6H), 5.14-5.12 (m, 1H), 3.56-3.51 (m, 1H), 3.33 (d, J=4.88 Hz, 1H), 2.37-2.29 (m, 1H), 2.18-0.86 (m, 18H), 1.06 (s, 9H), 0.99 (s 3H), 0.91 (s, 3H).

3β-(t-butyldiphenylsilyloxy)-17β-hydroxy-17α-(1,3,3-tribromoallyl)-5-androstene

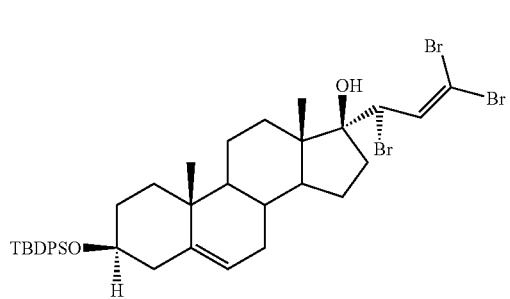

To a solution of (20S)-3β-(t-butyldiphenyl-silyloxy)-17β, 20-epoxy-5-androstene-21-carboxaldehyde (45 mg, 0.0792 mmol) in dry dichloromethane (2 mL) at 0° C. was added Ph₃P (113.8 mg, 0.434 mmol). After stirring for 10 minutes at 0° C. CBr₄ (70.78 mg, 0.213 mmol) was added. After stirring the reaction mixture for 1 hour at 0° C. water (1 mL) was added. The reaction mixture was extracted with dichloromethane and the organic layer was dried over anhydrous Na₂SO₄, then the solvent was evaporated in vacuo. The residue was purified by flash column chromatography (elution solvent: cyclohexane:EtOAc 98:2) to afford 3,8-(t-butyldiphenylsilyloxy)-17β-hydroxy-17α-(1,3,3-tribromo-allyl)-5-androstene. Yield 32.8 mg (52%); ¹H NMR (CDCl₃) δ: 7.68-7.66 (m, 4H), 7.41-7.36 (m, 6H), 7.08 (d, J=9.77 Hz, 1H), 5.11 (bs, 1H), 4.85 (d, J=10.37 Hz, 1H), 3.52 (bs, 1H), 2.43-0.87 (m, 19H), 1.06 (s, 9H), 0.99 (s 3H), 0.95 (s, 3H).

(20S)-3β-(t-butyldiphenylsilyloxy)-17β,20-epoxy-20-(2,2-dibromovinyl)-5-androstene

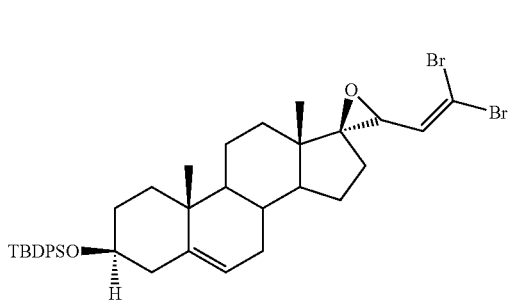

To a solution of 3β-(t-butyldiphenyl-silyloxy)-17β-hydroxy-17α-(1,3,3-tribromo-allyl)-5-androstene (32.8 mg, 0.04136 mmol) in dry THF (1 mL) was added at 0° C. TBAF (0.08271 mL of 1M sol. in THF, 0.08271 mmol). After stirring for 1 minute at 0° C. at this temperature, water (2 mL) was added to the reaction. The reaction mixture was extracted with diethylether and the organic layer was dried over anhydrous Na₂SO₄, then the solvent was evaporated in vacuo. The residue was pure enough to be carried further to the next reaction. Yield: 30 mg (quantitative); ¹H NMR (CDCl₃) δ: 7.69-7.65 (m, 4H), 7.44-7.33 (m, 6H), 6.19 (d, J=6.71 Hz, 1H), 5.14-5.12 (m, 1H), 3.75 (d, J=6.71 Hz, 1H), 3.59-3.47 (m, 1H), 2.38-2.29 (m, 1H), 2.16-2.10 (m, 1H), 1.99-1.92 (m, 1H), 1.79-0.85 (m, 16H), 1.05 (s, 9H), 0.99 (s 3H), 0.85 (s, 3H).

(20S)-3β-hydroxy-17β,20-epoxy-20-(2-bromoethynyl)-5-androstene

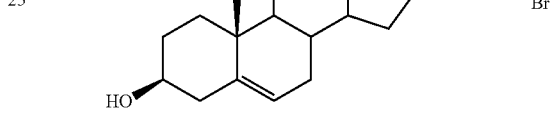

To a solution of (20S)-3β-(t-butyldiphenyl-silyloxy)-17β, 20-epoxy-20-(2,2-dibromovinyl)-5-androstene (30 mg, 0.04212 mmol) in dry THF (1 mL) at 0° C. was added TBAF 1 M sol. in THF (0.08424 mL, 0.08424 mmol). The reaction was stirred for 10 hours at room temperature and water was added. The reaction mixture was extracted with diethylether and the organic was dried over anhydrous Na₂SO₄, then the solvent was evaporated in vacuo. The residue was purified by flash column chromatography (elution solvent: cyclohexane:EtOAc 98:2) to afford (20S)-3β-hydroxy-17β,20-epoxy-20-(2-bromoethynyl)-5-androstene. Yield: 18 mg (quantitative); ¹H NMR (CDCl₃) δ: 5.37 (bs, 1H), 3.60-3.46 (m, 1H), 3.47 (s, 1H), 2.38-0.86 (m, 19H), 1.02 (s, 3H), 0.89 (s, 3H)

Example 4

Preparation of 3β,21-dihydroxy-17α,20-epoxy-5-pregnene (3β-Hydroxy-5-androstene-17-ylidene)-acetonitrile

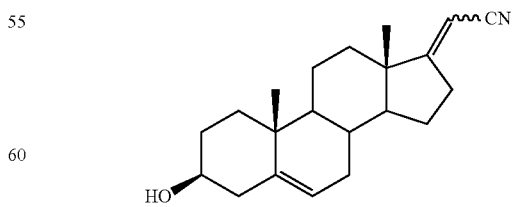

To a solution of t-BuOK (4.14 mmol, 465 mg) in dry THF (5 mL) at 0° C. was added diethyl cyanomethylphosphonate (2.76 mmol, 0.44 mL) and the reaction was stirred for 1 h. To the above mixture was added dropwise a solution of DHEA (0.69 mmol, 200 mg) in dry THF (5 mL) and the mixture was stirred at room temperature until completion of the reaction. The reaction was quenched by addition of saturated NH$_4$Cl and was extracted with ethyl acetate, and the organic layer was washed with brine and was dried over anhydrous Na$_2$SO$_4$, then the solvent was evaporated in vacuo. The residue was purified by flash column chromatography (elution solvent: petroleum ether:EtOAc 6:4) to afford the compound named above. Yield: 175 mg (81.5%).
$^1$H NMR (CDCl$_3$) δ: 5.28 (bs, 1H), 5.06 (s, 0,3H), 4.96 (s, 0.7H), 3.49-3.41 (m, 1H), 2.7-0.9 (m, 19H), 0.99 (s, 3H), 0.91 (s), 0.79 (s, 3H). $^{13}$C NMR (CDCl$_3$) δ: 180.9, 179.2, 141.1, 140.9, 120.9, 120.8, 117.4, 116.6, 87.9, 87.8, 71.3, 60.4, 55.2, 54.1, 49.9, 46.4, 45.9, 42.1, 37.2, 36.5, 34.5, 32.4, 31.5, 31.4, 30.2, 23.8, 20.8, 20.7, 19.4, 17.7, 16.6.

(3β-Hydroxy-5-androstene-17-ylidene)-acetaldehyde

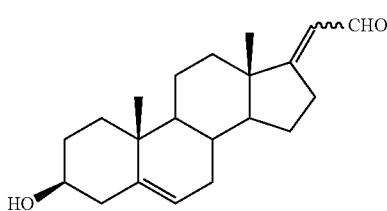 [SMILES: C[C@]12CC[C@H](O)CC1=CCC1C2CC[C@]2(C)C(=CC=O)CCC12]

To a solution of (3β-hydroxy-5-androstene-17-ylidene)-acetonitrile (150 mg, 0.48 mmol) in dry dichloromethane (15 mL) was added at -78° C. a solution of DIBAL-H (1M in dichloromethane, 1.44 mmol) and the reaction mixture was stirred for 30 min at -78° C. and for 5 hours at room temperature. The reaction mixture was diluted with dichloromethane and a solution of Na—K tartrate was added. The organic layer was extracted with brine and was dried over anhydrous Na$_2$SO$_4$, then the solvent was evaporated in vacuo. The residue was purified by flash column chromatography (elution solvent: Petroleum Ether:Acetone 8:2) to afford the compound named above. Yield: 151 mg (93%).
$^1$H NMR (CDCl$_3$) δ: 10.02 (d, J=8.54 Hz, 0.63H), 9.74 (d, J=7.93, 0.37H), 5.74-5.71 (m, 0.63H), 5.67-5.64 (m, 0.37H), 5.25-5.21 (m, 1H), 3.44-3.39 (m, 1H), 2.89-0.93 (m, 19H), 0.99 (s) and 0.93 (s) and 0.78 (s) (all three 6H); $^{13}$C NMR (CDCl$_3$) δ: 192.4, 190.7, 180.5, 179.4, 140.9, 124.0, 120.8, 119.3, 71.2, 65.0, 55.6, 53.3, 50.1, 49.4, 46.9, 46.3, 42.0, 38.6, 37.1, 36.6, 36.5, 36.4, 34.7, 33.5, 31.5, 31.3, 27.7, 24.3, 23.9, 21.3, 20.8, 19.3, 18.8, 17.8.

17-(2-hydroxy-ethylidene)-5-androstene-3β-ol

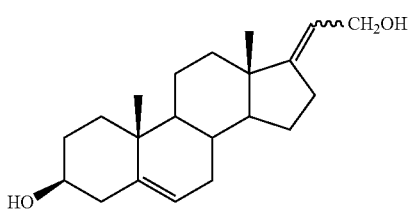 [SMILES: C[C@]12CC[C@H](O)CC1=CCC1C2CC[C@]2(C)C(=CCO)CCC12]

To a solution of 3β-hydroxy-5-androstene-17-ylidene)-acetaldehyde (0.24 mmol, 75 mg) in MeOH (2.5 mL) were sequentially added CeCl$_3$.7H$_2$O (0.24 mmol, 89 mg) and NaBH$_4$ (0.24 mmol, 10 mg). After completion of the reaction saturated NH$_4$Cl was added until pH 7. The mixture was diluted with ethyl acetate and the organic layer was extracted with brine and was dried over anhydrous Na$_2$SO$_4$, then the solvent was evaporated in vacuo. The residue was purified by flash column chromatography (elution solvent: Petroleum Ether:Acetone 8:2) to afford the compound named above. Yield: 70 mg (92%).
$^1$H NMR (CDCl$_3$) δ: 5.36-5.24 (m, 2H), 4.33-3.99 (m, 2H), 3.42-3.39 (m, 1H), 2.4-0.9 (m, 19H), 1.02 (s) and 0.94 (s) (both 3H), 0.90 (s) and 0.77 (s) both 3H.

3β,21-dihydroxy-17α,20-epoxy-5-pregnene

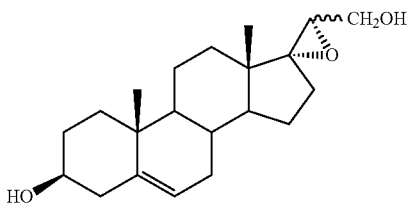

To a solution of 17-(2-hydroxy-ethylidene)-5-androstene-3β-ol (0.22 mmol, 70 mg) in dry dichloromethane (2.2 mL) were added K$_2$CO$_3$ (0.26 mmol, 36 mg) and m-chloroperoxybenzoic acid 55% (0.22 mmol, 61 mg), and the mixture was stirred at room temperature until completion of the reaction. The solid was filtered off and the filtrate was evaporated in vacuo and was purified by flash column chromatography (elution solvent: Petroleum Ether:ethyl acetate 1:1) to afford the compound named above in 75% yield.
$^1$H NMR (CDCl$_3$) δ: 5.36-5.34 (m, 1H), 3.90-3.53 (m, 3H), 3.15-3.11 (m, 1H), 2.4-0.9 (m, 19H), 0.99 (s, 3H), 0.83 (s, 3H).

Example 5

Preparation of
3β,22-dihydroxy-17β,21-oxetanyl-5-pregnene

17α-Allyl-5-androstene-3β,17β-diol

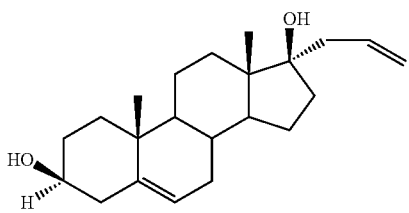 [SMILES: C=CC[C@]1(O)CCC2C3CC=C4C[C@@H](O)CC[C@]4(C)C3CC[C@@]21C]

To a solution of 3β-acetyl-5-androstene-17-one (200 mg, 0.6 mmol) in anhydrous tetrahydrofuran (4 mL) was added dropwise at 0° C. a solution of allyl magnesium bromide (1.7 M in tetrahydrofuran, 3.52 mL, 6 mmol) and the resulting mixture was stirred at room temperature for 12 h. After completion of the reaction saturated ammonium chloride was added and the resulting mixture was extracted with ethyl acetate. The organic layer was washed with brine, then dried with anhydrous Na$_2$SO$_4$ and the solvent was evaporated in vacuo. The residue was purified by flash column chromatography (elution solvent: cyclohexane/ethyl acetate 85:15), to obtain 17α-allyl-5-androstene-3β,17β-diol as a white crystalline solid.

Yield: 190 mg (95%).

3β,17β-dihydroxy-21,22-epoxy-5-androstene

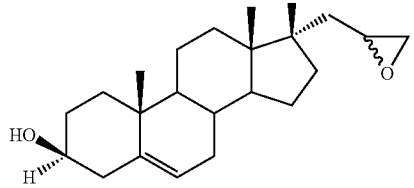

To a solution of 17α-allyl-5-androstene-3β,17β-diol (190 mg, 0.57 mmol) in anhydrous dichloromethane (6 mL), vanadium acetylacetonate (6.6 mg, 0.025 mmol) and t-butylhydroperoxide 70% (0.74 mL, 1.7 mmol) were sequentially added at −10° C. The resulting mixture was stirred at 0° C. for 12 h. After completion of the reaction the mixture was diluted with dichloromethane and the organic layer was extracted with $H_2O$, saturated $Na_2SO_3$ and brine and then was dried with anhydrous $Na_2SO_4$ after which the solvent was evaporated in vacuo. The residue was purified by flash column chromatography (elution solvent: dichloromethane/ethyl acetate 6:1), to obtain 3β,17β-dihydroxy-20,21-epoxy-5-androstene as a white crystalline solid. Yield: 69 mg (35%); $^1$H NMR (CDCl$_3$) δ: 5.35 (bs, 1H), 3.53 (m, 1H), 3.26 (m, 1H), 2.84-2.97 (m, 1H), 2.52-2.49 (m, 1H), 2.28-1.01 (m, H), 1.02 (s, 3H), 0.90 and 0.89 (s, 3H).

3β,22-dihydroxy-17β,21-oxetanyl-5-pregnene

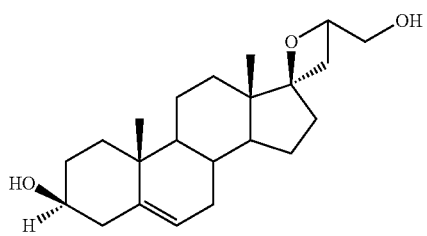

To a solution of 3β,17β-dihydroxy-21,22-epoxy-5-androstene (40 mg, 0.12 mmol) in anhydrous methylene chloride (12 mL) was added p-TsOH (0.6 mmol, 114 mg) and the resulting mixture was stirred at room temperature for 12 hours. After completion of the reaction the solid was removed by filtration and the filtrate was evaporated in vacuo. The residue was purified by flash column chromatography to afford the desired 17-spiro-oxetane derivative.

Example 6

Preparation of 17β-spiro-[3β-hydroxy-5-androsten-17,2'-oxiran-7-ylideneaminooxy]-acetic acid

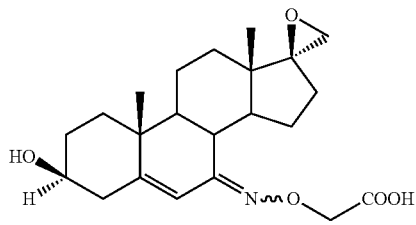 [SMILES: C[C@]12CC[C@H](O)CC1=CC(=NOCC(=O)O)C1C2CC[C@@]2(C)C1CC[C@@]21CO1]

To a solution of dehydroepiandrosterone-7-carboxymethyloxime (20 mg, 0.052 mmol) in anhydrous DMF (0.5 mL), trimethylsulfonium iodide (32 mg, 0.16 mmol) and t-BuOK (18 mg, 0.16 mmol) were added at 0° C., and the resulting mixture was stirred at room temperature for 10 hours. After completion of the reaction water was added, the solution was acidified to pH 5 with dilute HCl and the resulting mixture was extracted with dichloromethane. The organic layer was washed with brine, then dried with anhydrous $Na_2SO_4$ and the solvent was evaporated in vacuo. The residue was purified by flash column chromatography (elution solvent: petroleum ether 40°-60° C./acetone 8:2), to obtain the title compound.

Example 7

Use of Synthetic Spiro Neurosteroids to Protect Neural-Crest Derived PC12 Cells Against Serum-Deprivation Induced Cell Apoptosis Method Neural-crest derived PC12 cells were maintained in culture at 5% $CO_2$, at 37° C., in RPMI 1640 medium containing 2 mM L-glutamine, 15 mM HEPES, 100 units/ml penicillin, 0.1 mg/ml streptomycin, 10% horse serum, and 5% foetal calf serum. Serum free medium was supplemented with 1% bovine serum albumin (BSA). Different steroids, used at various concentrations, were initially diluted in ethanol. The final concentration of ethanol in each well, including controls was 0.01%. Conjugate DHEA-BSA was initially diluted in Phosphate Buffer Saline (PBS).

Cells were cultured in the absence of serum for 12 hours, supplemented with DHEA and various synthetic spiro neurosteroids at 10 nM. Cell apoptosis was quantitated with two different methods: *The APOPercentage Apoptosis Assay* (Biocolor Ltd., Belfast, N. Ireland) was used to quantify apoptosis, according to the manufacturer's instructions. Apoptosis was quantified following cell lysis by measuring the dye incorporated in apoptotic cells at 550 nm (reference filter 620 nm) using a colour filter microplate colorimeter (Dynatech MicroElisa reader, Chantilly, Va.) (see FIGS. 1 and 2). FACS Analysis: FACS analysis of apoptotic cells was performed according to our protocol (*Proc Natl Acad Sci USA* 101,8209 (2004)). Flow cytometry was performed with FACScan (Becton Dickinson, Heidelberg, Germany) and the results were analysed with the FACScan and Cell Quest softwares (see FIG. 3).

Figure 2:
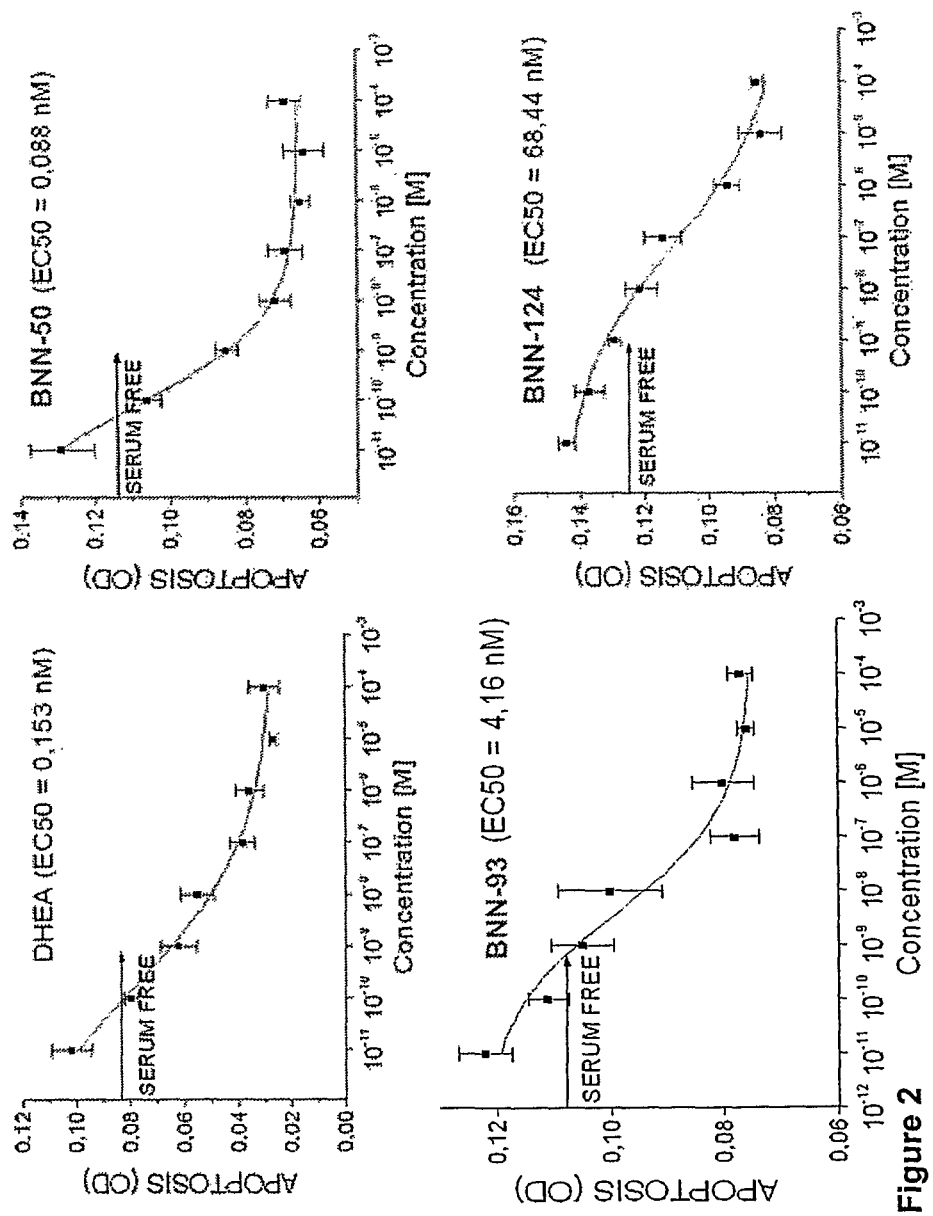
FIG. 2 consists of several graphs showing the dependence of apoptosis of neural-crest derived PC12 cells (as measured by optical density using a colorimeter) upon the concentration of several steroid compounds, in an experimental study using an assay technique.
Figure 3:
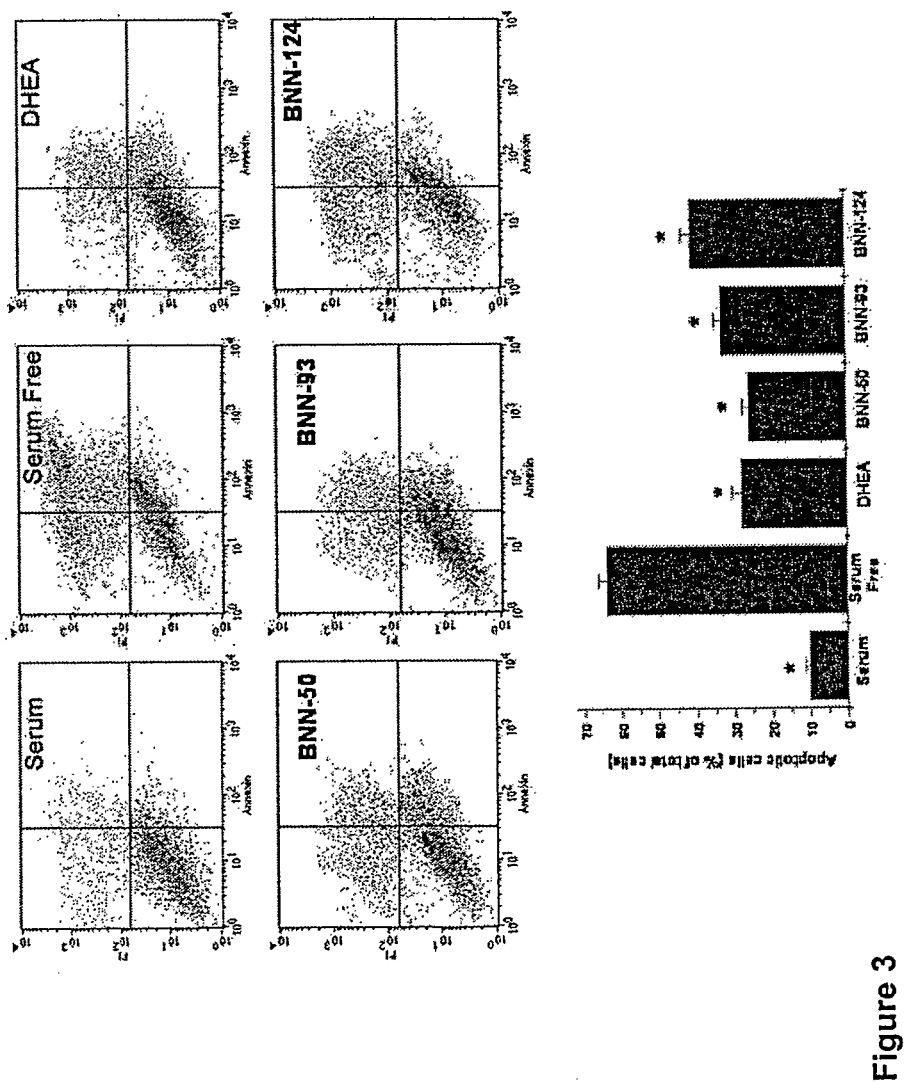
FIG. 3 shows the results of an experimental study utilising a FACS analysis of the effect of several steroid compounds on apoptosis of neural-crest derived PC12 cells.

Culture of PC12 cells in the absence of serum resulted in a strong induction of apoptosis, compared to cell cultures supplemented with serum, as shown with the ApoPercentage assay (FIG. 1). DHEA, non-permeable DHEA-BSA conjugate and spiro neurosteroids reversed serum deprivation-induced apoptosis by almost 50%, protecting PC12 cells from apoptosis, with $IC_{50}$ of 0.15 nM (FIG. 2). The synthetic 17-spiro neurosteroids also showed strong anti-apoptotic, cytoprotective effects with $IC_{50}$ of 0.088, 4.16 and 68.4 nM for BNN-50, BNN-93 and BNN-124 respectively (FIG. 2). The anti-apoptotic effects of synthetic spiro neurosteroids were also confirmed with FACS analysis (FIG. 3).

Example 8

Study of the Neuroprotective, Anti-Apoptotic Effects of Synthetic Spiro Neurosteroids by Induction of the Neuroprotective and Anti-Apoptotic Bcl-2 Proteins in Neural-Crest Derived PC12 Cells Method Neural-crest derived PC12 cells were cultured for 8 hours in the absence of serum, but supplemented with 10 nM of various neurosteroids. At the end of incubation cell lysates were subjected to electrophoresis through a 12% SDS-polyacrylamide gel. Then, proteins were transferred to nitrocellulose membranes, which were processed according to standard Western blotting procedures. To detect protein levels, membranes were incubated with the appropriate antibodies: Bcl-2, (Santa Cruz Biotechnology Inc., Santa Cruz, Calif., dilution 1:100) Bcl-xL (Cell Signalling Technology Inc., Beverly, Mass., dilution 1:100). A PC-based Image Analysis program was used to quantify the intensity of each band (Image Analysis, Inc., Ontario, Canada). To normalize for protein content, the blots were stripped and stained with anti-actin antibodies (Chemicon, Temecula, Calif., dilution 1:400); the concentration of each target protein was normalized versus actin.

Figure 4:
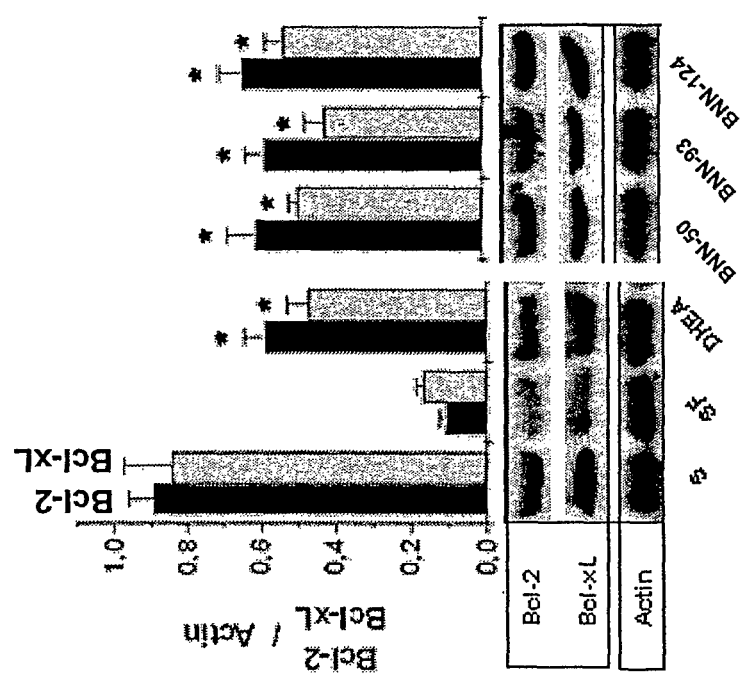
FIG. 4 shows the results of an experimental study of the effect of several steroid compounds on the levels of anti-apoptotic Bcl-2 and Bcl-xl proteins in neural-crest derived PC12 cells.

Results of these experiments are presented in FIG. 4. Serum deprivation (SF) of PC12 cells resulted in strong suppression of levels of anti-apoptotic Bcl-2 and Bcl-xL proteins. DHEA and all three synthetic spiro neurosteroids (BNN-50, BNN-93 and BNN-124) were preventing this effect as early as 12 h to levels comparable to those of serum supplementation (S).

Example 9

Study of the Neuroprotective, Anti-Apoptotic Effects of Synthetic Spiro Neurosteroids after Binding on DHEA Specific Membrane Receptors Method PC12 rat sympathoadrenal cells were cultured in 225 cm² flasks and, after washing twice with PBS, they were detached from the flasks by vigorous shaking. After a centrifugation at 1500 g, they were homogenized by sonication, in a 50 mM Tris-HCl buffer pH 7.4 at 4° C., containing freshly added protease inhibitors (1 mM PMSF and 1 µg/ml aprotinin). Unbroken cells were removed by centrifugation at 1500 g (10 min at 4° C.), and membranes were collected by centrifuging at 102,000 g for 1 hr at 4° C. Membranes were washed once with Tris-HCl, briefly acidified at 4° C. (for 3 min) with 50 mM glycine (pH 5.0), and re-suspended in the same buffer. Protein content was assayed by the method of Bradford, using reagents from Bio-Rad (Hercules, Calif.). Membranes (at a final concentration of 2 mg/ml) were incubated with 5 nM [³H]DHEA, in the absence (to determine the total binding) or presence of unlabeled neurosteroids and their synthetic spiro analogs, at concentrations varying from $10^{-12}$ to $10^{-6}$ M and at a final volume of 100 µl, in Tris-HCl buffer (50 mM, pH 7.4). Following a 30 mM incubation in a water bath, at 37° C., membranes were collected on GF/B filters, prewet in 0.5% PEI solution at 4° C. The filters were washed three times with ice-cold Tris-HCl, dried, supplemented with scintillation medium (Sigma Hellas, Athens, Greece) and counted in a β-scintillation counter (Perkin Elmer, Foster City, Calif.) with 60% efficiency for Tritium.

Figure 5:
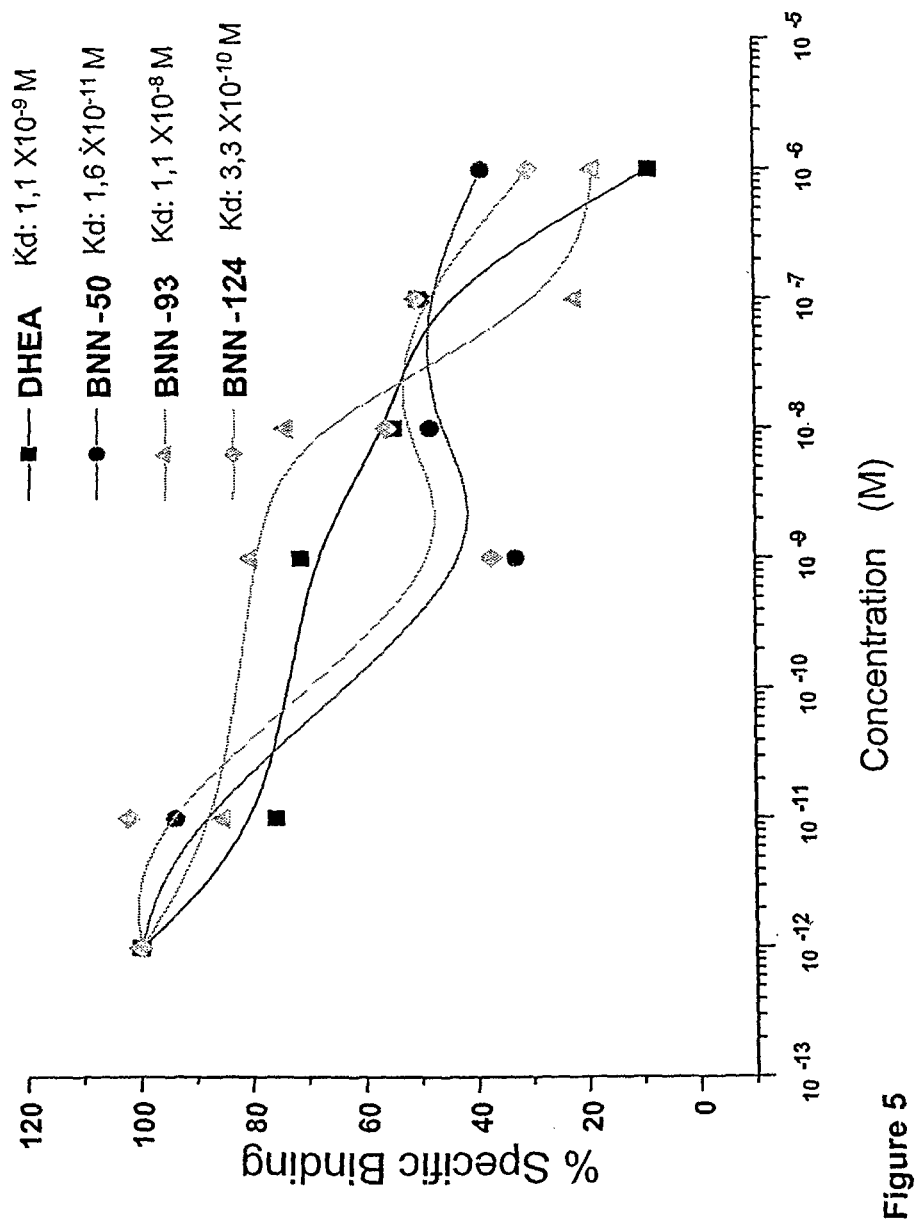
FIG. 5 shows the results of a concentration-dependent experimental study of the binding of several steroid compounds on the isolated membranes of PC12 rat sympathoadrenal cells.

Results are depicted in FIG. 5. Unlabeled DHEA competed for [³H]DHEA binding on isolated PC12 cell membranes with a $K_D$ of 1.1 nM. Almost complete competition was obtained at 1 µM (FIG. 5). Significant displacement (approximately 60% of specific binding at 1 µM) was documented by synthetic spiro neurosteroids BNN-50, BNN-93 and BNN-124, with apparent $K_D$ of 0.016, 11.2 and 0.33 nM respectively, indicating a strong interaction of all three synthetic neurosteroids with membrane DHEA binding.

Example 10

Study of Use of Synthetic Spiro Neurosteroids to Stimulate the Production and Secretion of Dopamine from Dopaminergic Neural Crest-Derived Cells Method Dopaminergic neural-crest derived PC12 cells were grown in 6-well plates, coated with poly-L-lysine, at a concentration of $10^6$ cells/well. Cells were incubated with neurosteroids or the vehicle for several time periods; for the short-term experiments the incubation time ranged from 5 to 30 minutes and for the long-term from 3 to 48 hours. 1 mL of supernatants were transferred to tubes containing 200 µl 0.1 M HCl for measurement of dopamine, which was measured by radioimmunoassay (TriCat™ RIA, RE29395, IBL Immuno Biological Lab., Hamburg, Germany) using $^{125}I$ as a tracer. The analytical sensitivity of the method was 30 pg/ml, its intra-assay CV was 9.5%, and its inter-assay CV was 16.7%. The cross reactivity between dopamine and norepinephrine was <0.013%

Tyrosine Hydroxylase (TH) RT-PCR: Total RNA was extracted from dopaminergic PC12 cells using the Trizol Reagent (Invitrogen Life technologies, CA). One microgram of total RNA was reverse transcribed by the Thermo-Script RT-PCR System (Invitrogen) using random hexamers in a total volume of 20 µl. Two microliters of the RT product was used as a template, amplified by PCR using 2 mM MgCl₂, one strength PCR buffer, 0.2 mM of sense and antisense primers, 0.2 mM dNTPs and 2.5 U AmpliTaq Gold DNA polymerase (Perkin Elmer ABD, Foster City, Calif.) in a final reaction volume of 50 µl. PCR was performed in a Perkin Elmer DNA Thermal Cycler. Primers for TH were 5'-TCGCCACAGCCCAAGGGCTTCAGAA-3' (sense), and 5-CCTCGAAGCGCACAAAATAC-3 (antisense) and for G3PDH were, 5'-TGAAGGTCGGAGTCAACG-GATTTGGT-3' (sense), and 5'-CATGTGGGCCATGAG-GTCCACCAC-3' (antisense). Oligonucleotides were synthesized by MWG-Biotech AG (Munich, Germany). After reverse transcription, the cDNA product was amplified by PCR, at 33 cycles. The cycle number (33) was chosen such that amplification of the products was in the linear range with respect to the amount of input cDNA. PCR for G3PDH was performed in parallel to assure good quality of RNA and cDNA preparations. Each cycle consisted of 60 s at 92° C.

for denaturation, 120 s at 53° C. for annealing, and 180 s at 72° C. for extension (60 s at 98° C., 90 s at 55° C., and 150 s at 72° C. for G3PDH respectively). 10 µl of the amplified products (368 bp for TH and 983 bp for G3PDH) were separated on a 2% agarose gel and visualized by ethidium bromide staining.

Figure 6:
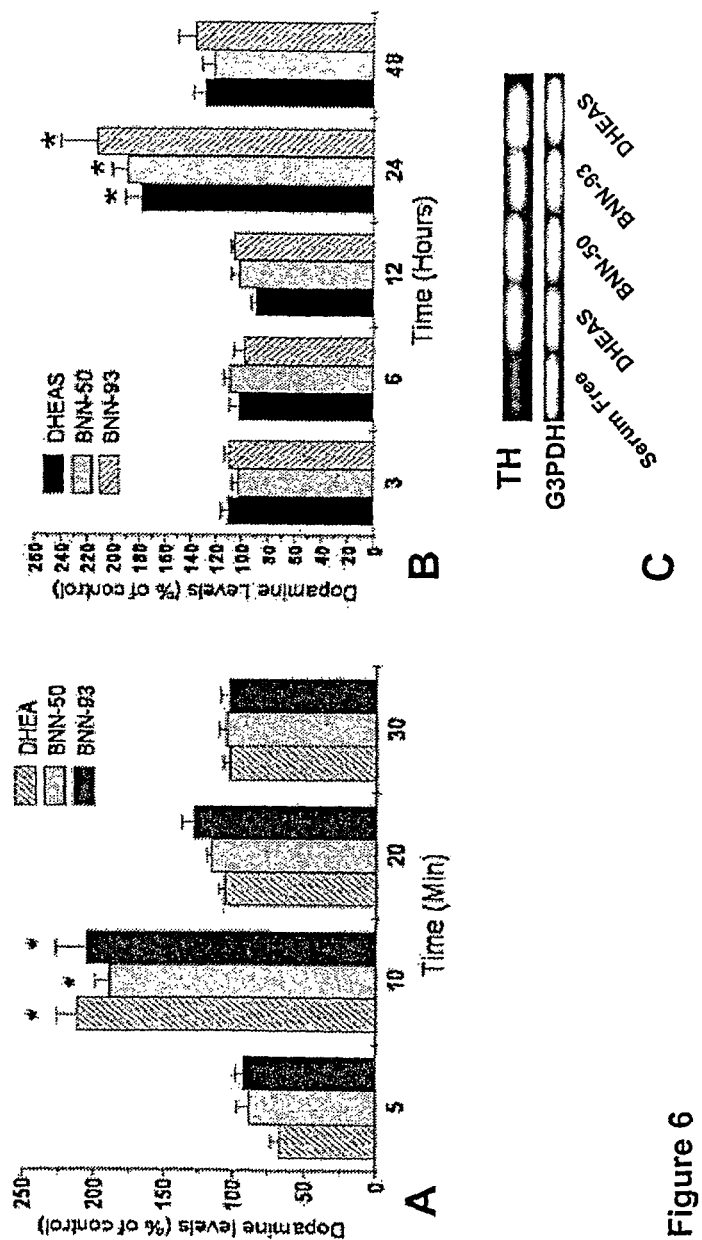
FIG. 6 shows the results of an experimental study of the effect of several steroid compounds on dopaminergic neural-crest derived PC12 cells.

Dopaminergic PC12 cells were exposed to DHEA, or to synthetic Spiro neurosteroids BNN-50 and BNN-93 ($10^{-7}$ M) for short periods of time (from 5 to 30 min) and the concentration of dopamine in culture media was measured using a radioimmunoassay, as described above. All three steroids tested provoked a fast and statistically significant stimulation of dopamine secretion, doubling their levels in the culture media within 10 min (see FIG. 6A). We have also tested the effect of steroids for longer periods of time. More specifically, PC12 cells were incubated with DHEAS, or with synthetic spiro neurosteroids BNN-50 and BNN-93 ($10^{-7}$ M) for 3 to 48 hours, and the concentration of dopamine in the culture media was measured. Incubation of PC12 cells with DHEAS or with synthetic neurosteroids resulted in an increase of dopamine levels peaking at 24 h (see FIG. 6B). These long-term effects of DHEAS and synthetic neurosteroids suggest that they may also, in addition to their acute effects on dopamine secretion (FIG. 6A), affect the de novo production of dopamine in dopaminergic neurons. Indeed, all three neurosteroids provoked a strong induction of the mRNA of the rate limiting enzyme of dopamine biosynthesis, tyrosine hydroxylase (see FIG. 6C).

Example 11

Neurogenic Properties of Synthetic Spiro Neurosteroids

Method

Primary cortical neurospheres (21d) generated from wild type mice were cultured attached on PLL and laminin-coated coverslips in serum-free media in the presence or absence of EGF and bFGF (20 ng/ml final concentration each). For the screen, the media was supplemented with ethanol, retinoic acid (at-RA), DHEA, or the synthetic spiro neurosteroid BNN-93, at a final concentration of $10^{-7}$M.

Figure 7:
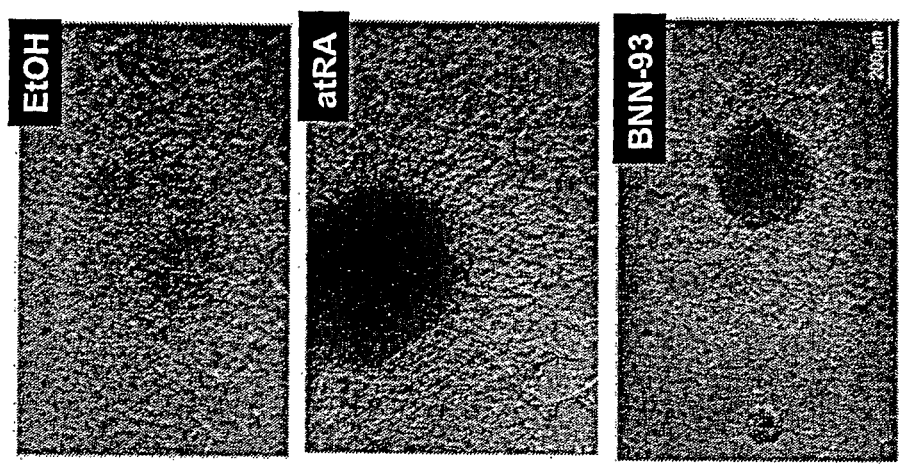
FIG. 7 shows the results of an experimental study of the effect of several compounds on primary cortical neurospheres generated from wild type mice.
Figure 8:
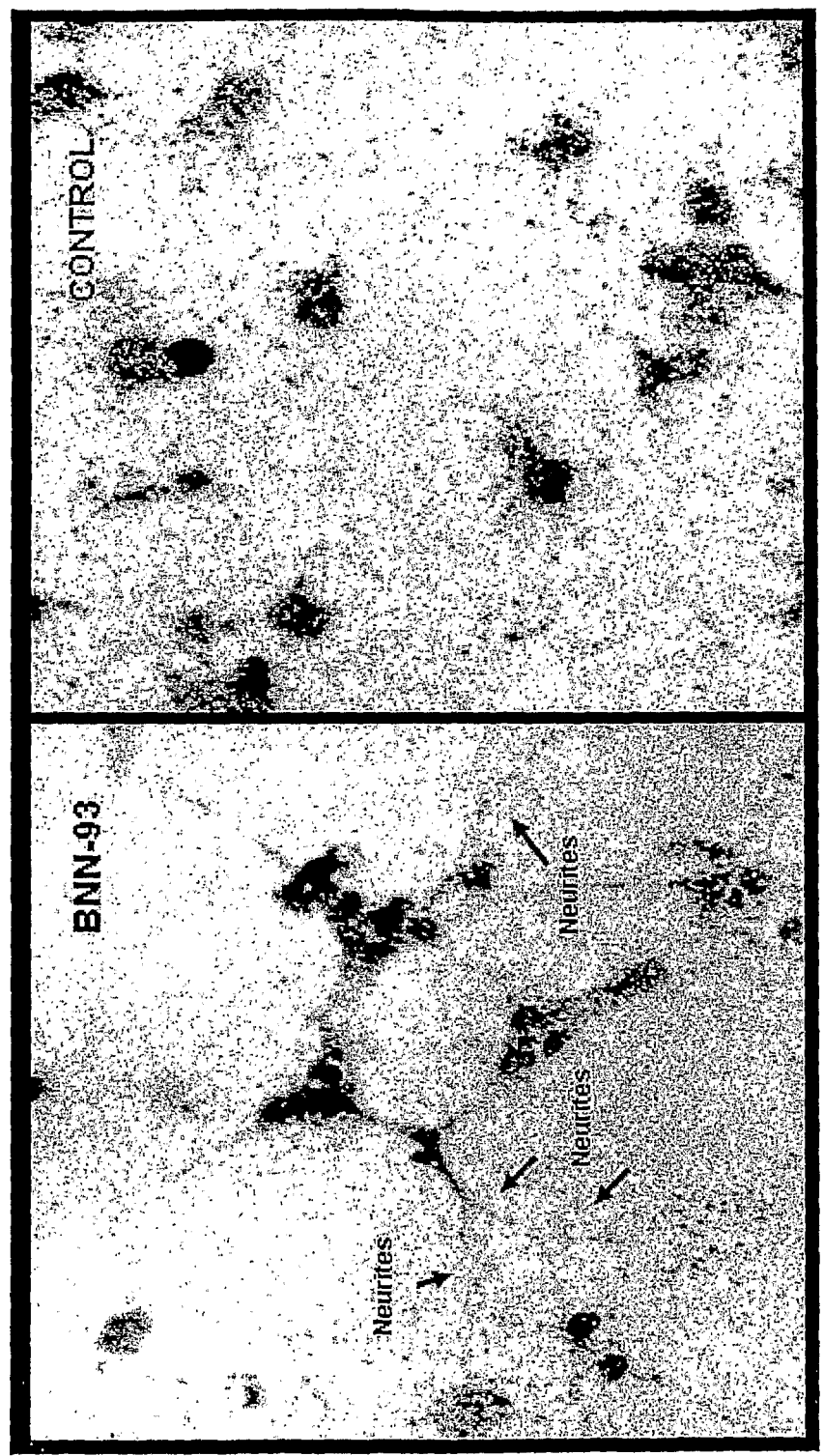
FIG. 8 shows the results of an experimental study of the effect of a synthetic neurosteroid on progenitor neural cells isolated from mouse fetal brain, compared with a control.

Within 24-48 hrs of culture, neurospheres supplemented with BNN-93 and DHEA demonstrated extensive migration of neural cells to the periphery of the neurospheres compared to the other compounds and the ethanol control (see FIG. 7). This effect appeared to be EGF/bFGF dependent. By day 6, all neurospheres cultured showed the same extent of migration of neural cells on the coverslip. The extent of migration of the first days in culture was mostly normalised as in most conditions cells had migrated out of the sphere to the periphery. The photographs shown (FIG. 7) were obtained on the $6^{th}$ day of culture where migration effects are not so dramatic but still evident. Additionally, progenitor neural cells, isolated from mouse fetal brain, were exposed for 24 hours to 100 nM of BNN-93 or to the vehicle (control). BNN-93 stimulated neurogenesis and differentiation of progenitors to neural cells, propagating the formation of neurites (see FIG. 8, arrows).

Example 12

Estrogenic Properties of Synthetic Spiro Neurosteroids

Treatment of postmenopausal syndromes with 17β-estradiol (E2) is associated with a higher risk of developing breast and/or endometrial cancer (*Arch Intern Med.* 166, 1027 (2006)). E2 stimulation of the proliferation of cancer cells is driven by estrogen receptor alpha (ERα) (*Mol. Endocrinol.* 13, 969 (1999)). Since BNN-50, BNN-93 and BNN-124 may form two hydrogen bonds with an O—O distance of 10.9-12.5 Å and thus may fit the ERα binding cavity (*Chem. Biol.* 11, 397 (2004)), it was imperative to examine the estrogen agonism/antagonism properties of these neurosteroids using human adenocarcinoma cells from breast (MCF-7 cells) and uterus (Ishikawa cells) as reporters. Full estrogen agonism (E2 at ≥0.1 nM) and non-agonism (vehicle only) controls served to classify the neurosteroids as super, full, partial, weak and marginal agonists depending on whether their estrogenic efficacy was >100, 76-100, 26-75, 10-25 and 1-10% of that of E2 (set equal to 100). Similarly, full antagonism of the effect of E2 (at 0.1 nM) by ICI 182, 780 (at ≥10 nM) and non-antagonism (vehicle only) controls served to classify the neurosteroids as full, partial, weak and marginal antagonists depending on whether their suppression of the effect of E2 was 76-100, 26-75, 10-25 and 1-10% of that of ICI 182, 780. Differences between control and neurosteroid-treated cells were assessed using one-way ANOVA. Significance was accepted for values of $p<0,05$.

Methods

To determine neurosteroid effects on the growth of MCF-7 human mammary (from ATCC) and Ishikawa endometrial adenocarcinoma cells (from ECACC), the cells were cultured at 37° C. in Dulbecco's Minimal Essential Medium (DMEM) supplemented with 10% Fetal Bovine Serum (FBS, from Biochrom) in 5% $CO_2$ and subcultured using a trypsin 0.25%-EDTA 0.02% solution. Neurosteroid effects on the growth of the cells were assessed using MTT [3-(4, 5-dimethylthiazol-2-yl)-2,5-diphenyltetrazolium bromide] and standard methodology (*Chem. Biol.* 11, 397 (2004)). Briefly, cells were plated in 96-well flat-bottomed microplates at a density of 10,000 cells/well, in phenol-red-free medium supplemented with 1% dextran-coated-charcoal-treated FBS (DCC-FBS). 24 hours later, serial dilutions of test compounds were added (initial dilution in DMSO, further dilutions in culture medium), fresh media with test compounds added every 48 hours, and after 6 days the medium was removed and the cells were incubated with 1 mg/ml MTT (from Sigma) in serum-free, phenol-red-free medium for 4 hours. The MTT-formazan that was produced was solubilized in isopropanol and measured by monitoring absorbance at 550 nm vs. 690 nm using a Safire plate reader (from Tecan). Cells that received only medium served as non-agonism controls, while those treated with ICI 182, 780 (from Tocris) and/or E2 (from Sigma) served as full antagonism and agonism controls, respectively.

To determine neurosteroid effects on E2 induction of the alkaline phosphatase activity of Ishikawa cells—a very sensitive means of detecting E2 agonists/antagonists among natural and commodity chemicals (*Planta Med.* 72, 488 (2006))—cells were cultured and subcultured as described above. Cells were then plated in 96-well flat-bottomed microculture plates at a density of 12,000 cells per well in phenol-red-free medium supplemented with 5% DCC-FBS. 24 hours later fresh medium was added followed by test compounds (initial dilution in DMSO, further dilutions in culture medium), the cells were cultured for 72 h, they were then washed with PBS and the plates were inverted, blotted gently on a paper towel, placed at −80° C. for at least 15 min, thawed at room temperature for 5-10 min, and then transferred onto ice. Next, 500 ice-cold solution containing 5 mM p-nitrophenyl phosphate, 0.24 mM $MgCl_2$, and 1M diethanolamine (pH 9.8) were added, the cells were warmed to room temperature (time zero), and yellow colored p-nitrophenol was allowed to accumulate with time. Cells that received only medium served as non-agonism controls, while those treated with ICI 182, 780 and/or E2 served as full antagonism and agonism controls, respectively. The color was monitored every 30 min at 405 nm using the Safire plate reader until positive controls showed an absorbance ($A_{405}$) of about 1.2. The estrogen agonist/antagonist character of the Spiro neurosteroids in the different test systems is reported in Table 1.

TABLE 1 estrogen agonism/antagonism of BNN-50

| Estrogenic response | E2 agonism (at 1 uM) | E2 antagonism (at 1 uM) |
| --- | --- | --- |
| MCF-7 cell growth | non-significant | non-significant |
| Ishikawa cell growth | non-significant | non-significant |
| Ishikawa AlkP | non-significant | marginal |

Example 13

Study of the Binding, Activating or Inhibiting Capacity of Synthetic Spironeurosteroids on Nerve Growth Factor Receptors TrkA and p75NTR Method HEK293 cells were transfected with the cDNAs of TrkA and p75NTR, the high and low affinity receptors for nerve growth factor (NGF) (Ann Rev Biochem 72:604, 2003). Transfectants expressing the two NGF receptor subtypes were cultured in flasks and, after washing twice with PBS, they were detached from the flasks. After a centrifugation at 1500 g, they were homogenized by sonication, in a 50 mM Tris-HCl buffer pH 7.4 at 4° C., containing freshly added protease inhibitors (1 mM PMSF and 1 µg/ml aprotinin). Unbroken cells were removed by centrifugation at 1500 g (10 min at 4° C.), and membranes were collected by centrifuging at 102,000 g for 1 hr at 4° C. Membranes were washed once with Tris-HCl, briefly acidified at 4° C. (for 3 min) with 50 mM glycine (pH 5.0), and re-suspended in the same buffer. Protein content was assayed by the method of Bradford, using reagents from Bio-Rad (Hercules, Calif.). Membranes (at a final concentration of 2 mg/ml) were incubated with 5 nM [$^3$H]DHEA, in the absence (to determine the total binding) or presence of unlabelled BNN-124 at concentrations varying from $10^{-12}$ to $10^{-6}$ M and at a final volume of 100 µl, in Tris-HCl buffer (50 mM, pH 7.4). Following 30 min incubation in a water bath at 37° C., membranes were collected on GF/B filters, prewet in 0.5% PEI solution at 4° C. The filters were washed three times with ice-cold Tris-HCl, dried and counted in a β-scintillation counter (Perkin Elmer, Foster City, Calif.) with 60% efficiency for tritium.

Figure 9:
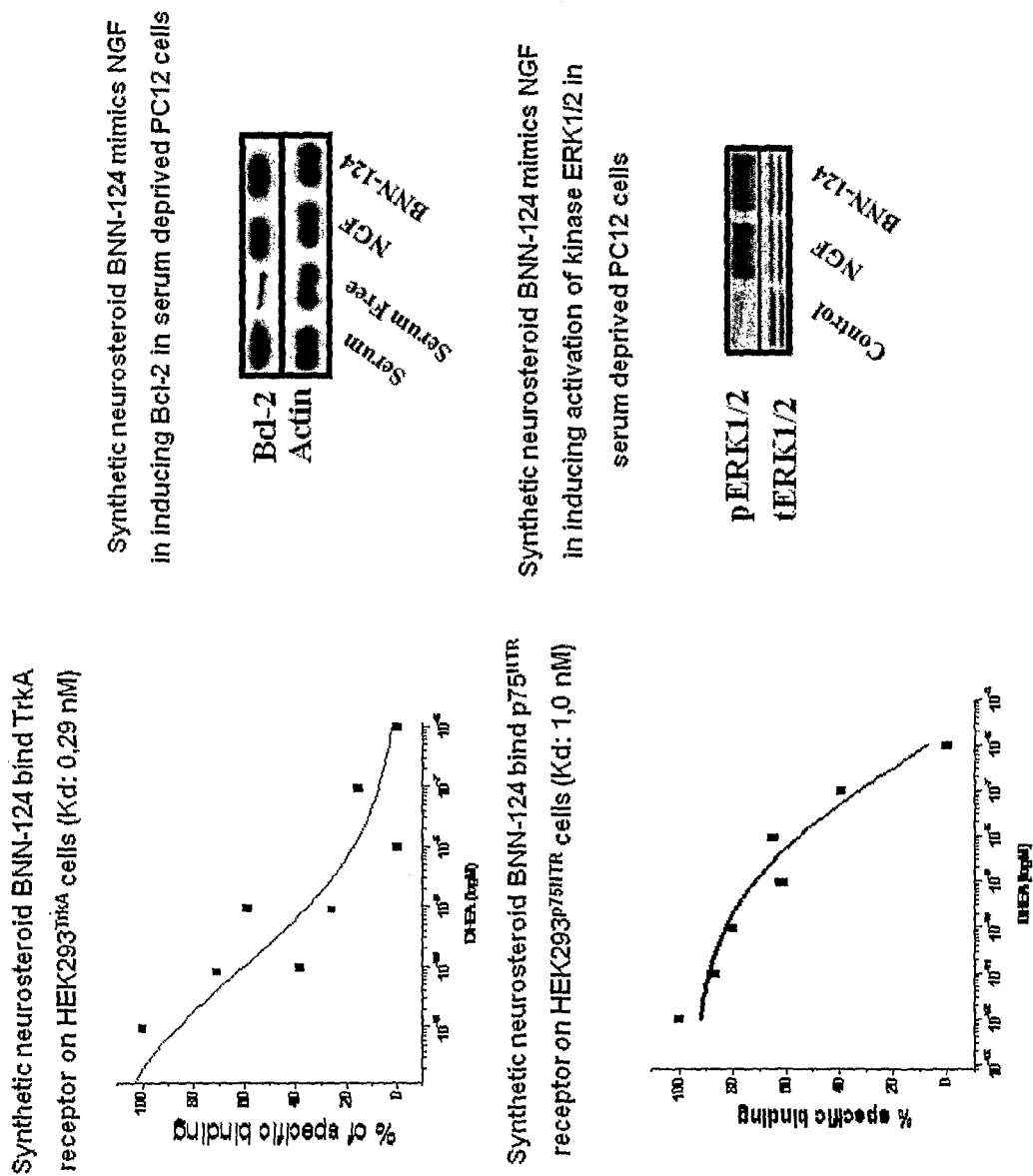
FIG. 9 shows the results of an experimental study of the binding, activating or inhibiting capacity of a synthetic neurosteroid on nerve growth factors in transfected HEK293 cells.

The results are depicted in FIG. 9. Unlabelled BNN-124 competed for [$^3$H]DHEA binding on isolated membranes from HEK293 TrkA cells, expressing TrkA NGF receptors. The affinity of this binding was $K_D$: 0.29 nM, i.e. similar to that of NGF. Similarly, unlabelled BNN-124 competed for [$^3$H]DHEA binding on isolated membranes from HEK293 p75NTR cells expressing p75NTR NGF receptors. The affinity of this binding was $K_D$: 1.0 nM, i.e. similar to that of NGF. No binding was shown in HEK293 cells transfected with the vector empty of TrkA cDNA or non-transfected cells. Furthermore, membrane staining of HEK293 cells transfected with the TrkA cDNA was shown with membrane impermeable DHEA-BSA-Fluorescein conjugate. These findings indicate a strong binding and interaction of synthetic spiro-neurosteroids with membrane NGF receptors.

Neural-crest derived PC12 cells were cultured for 8 hours in the absence of serum, but supplemented with 10 nM of synthetic neurosteroids of 20 ng/ml of NGF. At the end of incubation cell lysates were subjected to electrophoresis through a 12% SDS-polyacrylamide gel. Then proteins were transferred to nitrocellulose membranes, which were processed according to standard Western blotting procedures. To detect protein levels, membranes were incubated with the appropriate antibodies: Bcl-2 (Santa Cruz Biotechnology Inc., Santa Cruz, Calif., dilution 1:100), phosphorylated ERK1/2 (Cell Signalling Technology Inc., Beverly, Mass., dilution 1:100). To normalize for protein content, the blots were stripped and stained with anti-actin or anti-total ERK1/2 antibodies (Chemicon, Temecula, Calif., dilution 1:400).

The behaviour of BNN-124 mimicked that of NGF in inducing the anti-apoptotic Bcl-2 protein and the phosphorylation of ERK1/2 kinase in serum deprived PC12 cells. Indeed, 10 nM of BNN-124 produced the same effect on both Bcl-2 and ERK1/2 with 20 ng/ml of NGF (FIG. 9). Bcl-2 activation by NGF rescues neurons from apoptosis, an effect which is mediated by the activation through phosphorylation of ERK1/2 kinase signalling.

The invention claimed is:

1. A compound represented by Formula I

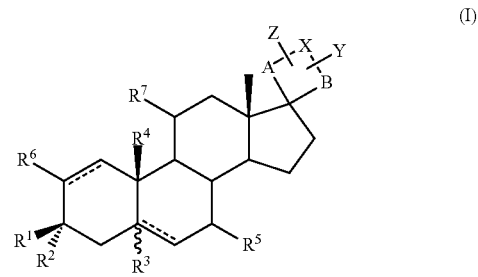

wherein
$R^1$=OH; $R^2$=$R^5$=$R^6$=$R^7$=Y=H; and $R^4$=Me;
a double bond is present between C5 and C6 of the steroid ring system, so that $R^3$ is not present;
X is an oxygen atom;
A is —(CH$_2$)$_n$—, a C$_{2-5}$ alkenylene group, or a C$_{2-5}$ alkynylene group, wherein n is an integer with a value of 0 or 1 or 2 or 3 or 4 or 5;
B is —(CH$_2$)$_y$—, a C$_{2-5}$ alkenylene group, or a C$_{2-5}$ alkynylene group, wherein y is an integer with a value of 1or 2 or 3 or 4 or 5;
Z is bonded to any carbon of the spirocyclic substituent at C17 of the steroid skeleton and is independently a substituted C$_{1-10}$ alkyl, an optionally substituted fused bicyclic ring system, an optionally substituted bridged bicyclic ring system, an optionally substituted bridged tricyclic ring system, optionally substituted C$_{2-10}$ alkenyl, substituted C$_{2-10}$ alkynyl, optionally substituted aryl, optionally substituted arylalkyl, optionally substituted heteroaryl, optionally substituted heteroarylalkyl, formyl, carboxy, —NC(O)R$^8$, NC(S)R$^8$, —NR$^8$R$^9$, optionally substituted C(O)—W, optionally substituted C(O)O—W, or optionally substituted C(S)O—W;
Y and Z are optionally bonded to the same carbon of the spirocyclic substituent at C17;

W is optionally substituted $C_{1-10}$ alkyl, optionally substituted heterocycloalkyl, an optionally substituted fused bicyclic ring system, an optionally substituted bridged bicyclic ring system, an optionally substituted bridged tricyclic ring system, optionally substituted $C_{2-10}$alkenyl, optionally substituted heterocycloalkenyl, optionally substituted $C_{2-10}$ alkynyl, optionally substituted heterocycloalkynyl, optionally substituted aryl, or optionally substituted heteroaryl;

$R^8$ and $R^9$ are independently optionally substituted $C_{1-10}$ alkyl, optionally substituted heterocycloalkyl, an optionally substituted fused bicyclic ring system, an optionally substituted bridged bicyclic ring system, an optionally substituted bridged tricyclic ring system, optionally substituted $C_{2-10}$ alkenyl, optionally substituted heterocycloalkenyl, optionally substituted $C_{2-10}$ alkynyl, optionally substituted heterocycloalkynyl, optionally substituted aryl, or optionally substituted heteroaryl;

and the dotted lines indicate that a single or double bond is present;

or a pharmaceutically acceptable salt or acid addition salt thereof;

but not including compounds of Formula I wherein:
A=—$(CH_2)_n$—; B=—$(CH_2)_y$—; no double bond is present between C1 and C2 of the steroid ring system; Z=2-pyridyl; n=0; and y=1.

2. A compound according to claim 1 wherein A=—$(CH_2)_n$—; B=—$(CH_2)_y$—; no double bond is present between C1 and C2 of the steroid ring system; n=0; and y=1.

3. A compound according to claim 1 selected from:
(20S)-3β,21-dihydroxy-17β,20-epoxy-5-pregnene;
(20S)-3β-hydroxy-17β,20-epoxy-20-(2-bromoethynyl)-5-androstene;
3β,21-dihydroxy-17α,20-epoxy-5-pregnene; and
pharmaceutically acceptable salts and acid addition salts thereof.

4. A composition comprising a compound of formula I as defined in claim 1 or a pharmaceutically acceptable salt or acid addition salt thereof, as an active ingredient together with a pharmaceutically acceptable carrier, diluent, or adjuvant.

* * * * *